US011810685B2

(12) United States Patent
Nunn

(10) Patent No.: US 11,810,685 B2
(45) Date of Patent: Nov. 7, 2023

(54) EARLY DETECTION OF RADIOISOTOPE GENERATOR END LIFE

(71) Applicant: BRACCO DIAGNOSTICS INC., Monroe Township, NJ (US)

(72) Inventor: Adrian Nunn, Lambertville, NJ (US)

(73) Assignee: Bracco Diagnostics Inc., Monroe Township, NJ (US)

( * ) Notice: Subject to any disclaimer, the term of this patent is extended or adjusted under 35 U.S.C. 154(b) by 618 days.

(21) Appl. No.: 17/042,355

(22) PCT Filed: Mar. 28, 2019

(86) PCT No.: PCT/US2019/024515
§ 371 (c)(1),
(2) Date: Sep. 28, 2020

(87) PCT Pub. No.: WO2019/191386
PCT Pub. Date: Oct. 3, 2019

(65) Prior Publication Data
US 2021/0020322 A1  Jan. 21, 2021

Related U.S. Application Data

(60) Provisional application No. 62/649,556, filed on Mar. 28, 2018.

(51) Int. Cl.
G21G 1/00 (2006.01)
A61B 6/00 (2006.01)
(Continued)

(52) U.S. Cl.
CPC ......... *G21G 1/0005* (2013.01); *A61B 6/4057* (2013.01); *A61B 6/4258* (2013.01);
(Continued)

(58) Field of Classification Search
CPC .. G21G 1/0005; A61B 6/4057; A61B 6/4258; A61M 5/1408; A61M 5/16827; A61M 2205/18; A61M 2205/702; G01T 1/167
See application file for complete search history.

(56) References Cited

U.S. PATENT DOCUMENTS 3,483,867 A  12/1969  Markovitz
3,535,085 A  10/1970  Shumate
(Continued)

FOREIGN PATENT DOCUMENTS

AT        399241 B    4/1995
CA     2913373 A1     4/2008
(Continued)

OTHER PUBLICATIONS 337-1110_ 662084: Complainant Bracco Diagnostics Inc.'s Response to Jubilant's Motion for Summary Determination of Noninfringement of U.S. Pat. Nos. 9,750,869, 9,750,870, and 9,814,826 by Jubilant's Version 3.1 and Version 4 Designs and Memorandum in Support Thereof (Motion Response/Reply); 2-1386970: "Disputes to Chart of Material Facts", create date Nov. 19, 2018, www.edis.usitc.gov.

(Continued)

*Primary Examiner* — Nicole M Ippolito
*Assistant Examiner* — Hanway Chang
(74) *Attorney, Agent, or Firm* — Fredrikson & Byron, P.A.

(57) ABSTRACT

An infusion system (10) including a radioisotope generator (52) that generates a radioactive eluate via an elution, an activity detector (58) configured to measure an activity of a first radioisotope in the radioactive eluate generated by the radioisotope generator, and a controller (80). The controller can track a cumulative volume of radioactive eluate generated by the radioisotope generator and also track the activity (Continued)

of the first radioisotope in the radioactive eluate generated by the radioisotope generator. The controller can determine a predicted volume of the radioactive eluate generated by the radioisotope generator at which the activity of the first radioisotope in the radioactive eluate will reach a threshold based on the tracked cumulative volume of the radioactive eluate and the tracked activity of the first radioisotope. This information can be useful for proactively removing the radioisotope generator from service and/or replacing the radioisotope generator with a fresh generator.

32 Claims, 9 Drawing Sheets

(51) Int. Cl.
*A61M 5/14* (2006.01)
*A61M 5/168* (2006.01)
*G01T 1/167* (2006.01)

(52) U.S. Cl.
CPC ...... *A61M 5/1408* (2013.01); *A61M 5/16827* (2013.01); *G01T 1/167* (2013.01); *A61M 2205/18* (2013.01); *A61M 2205/702* (2013.01)

(56) References Cited

U.S. PATENT DOCUMENTS

| | | |
|---|---|---|
| 3,543,752 A | 12/1970 | Hesse et al. |
| 3,565,376 A | 2/1971 | Viers |
| 3,576,998 A | 5/1971 | Deutsch et al. |
| 3,710,118 A | 1/1973 | Holgate et al. |
| 3,714,429 A | 1/1973 | Mozley et al. |
| 3,767,915 A | 10/1973 | Battist |
| 3,774,036 A | 11/1973 | Gerhart |
| 3,847,138 A | 11/1974 | Gollub |
| 3,861,380 A | 1/1975 | Chassagne |
| 3,953,567 A | 4/1976 | Grant et al. |
| 3,991,960 A | 11/1976 | Tanaka |
| 3,997,784 A | 12/1976 | Picunko et al. |
| 4,096,859 A | 6/1978 | Agarwal et al. |
| 4,160,910 A | 7/1979 | Thornton et al. |
| 4,212,303 A | 7/1980 | Nolan |
| 4,239,970 A | 12/1980 | Eckhardt et al. |
| 4,241,728 A | 12/1980 | Mirell |
| 4,286,169 A | 8/1981 | Rossem |
| 4,336,036 A | 6/1982 | Leeke et al. |
| 4,406,877 A | 9/1983 | Neirinckx et al. |
| 4,466,888 A | 8/1984 | Verkaart |
| 4,562,829 A | 1/1986 | Bergner |
| 4,585,009 A | 4/1986 | Barker et al. |
| 4,585,941 A | 4/1986 | Bergner |
| 4,597,951 A | 7/1986 | Gennaro et al. |
| 4,623,102 A | 11/1986 | Hough, Jr. |
| 4,624,661 A | 11/1986 | Arimond |
| 4,625,118 A | 11/1986 | Kriwetz et al. |
| 4,656,697 A | 4/1987 | Naeslund |
| 4,674,403 A | 6/1987 | Bryant et al. |
| 4,679,142 A | 7/1987 | Lee |
| 4,755,679 A | 7/1988 | Wong |
| 4,759,345 A | 7/1988 | Mistry |
| 4,769,008 A | 9/1988 | Hessel |
| 4,847,505 A | 7/1989 | Suthanthiran |
| 4,853,546 A | 8/1989 | Abe et al. |
| 4,859,431 A | 8/1989 | Ehrhardt |
| 4,994,056 A | 2/1991 | Ikeda |
| 5,039,863 A | 8/1991 | Matsuno et al. |
| 5,092,834 A | 3/1992 | Bradshaw et al. |
| 5,115,407 A | 5/1992 | Bird et al. |
| 5,166,526 A | 11/1992 | Dietzel |
| 5,223,434 A | 6/1993 | Kanno et al. |
| 5,254,328 A | 10/1993 | Herscheid et al. |
| 5,258,906 A | 11/1993 | Kroll et al. |
| 5,265,133 A | 11/1993 | Matthews |
| 5,274,239 A | 12/1993 | Lane et al. |
| 5,284,481 A | 2/1994 | Soika et al. |
| 5,395,320 A | 3/1995 | Padda et al. |
| 5,468,355 A | 11/1995 | Shefer et al. |
| 5,475,232 A | 12/1995 | Powers et al. |
| 5,483,070 A | 1/1996 | Valenta |
| 5,485,831 A | 1/1996 | Holdsworth et al. |
| 5,573,747 A | 11/1996 | Lacy |
| 5,580,541 A | 12/1996 | Wells et al. |
| 5,590,648 A | 1/1997 | Mitchell et al. |
| 5,674,404 A | 10/1997 | Kenley et al. |
| 5,681,285 A | 10/1997 | Ford et al. |
| 5,702,115 A | 12/1997 | Pool |
| 5,739,508 A | 4/1998 | Uber, III |
| 5,765,842 A | 6/1998 | Phaneuf et al. |
| 5,827,429 A | 10/1998 | Ruschke et al. |
| 5,840,026 A | 11/1998 | Uber, III et al. |
| 5,885,216 A | 3/1999 | Evans, III et al. |
| 5,971,923 A | 10/1999 | Finger |
| 6,058,718 A | 5/2000 | Forsberg et al. |
| 6,157,036 A | 12/2000 | Whiting et al. |
| 6,220,554 B1 | 4/2001 | Daoud |
| 6,267,717 B1 | 7/2001 | Stoll et al. |
| 6,269,810 B1 | 8/2001 | Brooker et al. |
| 6,327,895 B1 | 12/2001 | Jeppsson et al. |
| 6,347,711 B1 | 2/2002 | Goebel et al. |
| 6,442,418 B1 | 8/2002 | Evans et al. |
| 6,450,936 B1 | 9/2002 | Smith et al. |
| 6,454,460 B1 | 9/2002 | Ramanathan et al. |
| 6,558,125 B1 | 5/2003 | Futterknecht |
| 6,626,862 B1 | 9/2003 | Duchon et al. |
| 6,639,237 B2 | 10/2003 | Pedersen et al. |
| 6,673,594 B1 | 1/2004 | Owen et al. |
| 6,758,975 B2 | 7/2004 | Peabody et al. |
| 6,767,319 B2 | 7/2004 | Reilly et al. |
| 6,773,686 B1 | 8/2004 | Herscheid et al. |
| 6,787,030 B2 | 9/2004 | Hsi et al. |
| 6,870,175 B2 | 3/2005 | Dell et al. |
| 6,901,283 B2 | 5/2005 | Evans, III et al. |
| 6,908,598 B2 | 6/2005 | Sylvester |
| 6,931,327 B2 | 8/2005 | Goode, Jr. et al. |
| 7,091,494 B2 | 8/2006 | Weisner et al. |
| 7,125,166 B2 | 10/2006 | Eck et al. |
| 7,163,031 B2 | 1/2007 | Graves et al. |
| 7,169,135 B2 | 1/2007 | Duchon et al. |
| 7,204,797 B2 | 4/2007 | Reilly et al. |
| 7,256,888 B2 | 8/2007 | Staehr et al. |
| 7,286,867 B2 | 10/2007 | Schlyer et al. |
| 7,413,123 B2 | 8/2008 | Ortenzi |
| 7,476,377 B2 | 1/2009 | Moller et al. |
| 7,504,646 B2 | 3/2009 | Balestracci et al. |
| 7,522,952 B2 | 4/2009 | Krieg et al. |
| 7,586,102 B2 | 9/2009 | Mourtada et al. |
| 7,605,384 B2 | 10/2009 | Sonnenhol et al. |
| 7,608,831 B2 | 10/2009 | Lamb et al. |
| 7,612,999 B2 | 11/2009 | Clark et al. |
| 7,712,491 B2 | 5/2010 | Tochon-Danguy et al. |
| 7,734,331 B2 | 6/2010 | Dhawale et al. |
| 7,737,415 B2 | 6/2010 | Casale et al. |
| 7,780,352 B2 | 8/2010 | Fox et al. |
| 7,804,415 B2 | 9/2010 | Cheng et al. |
| 7,813,841 B2 | 10/2010 | deKemp et al. |
| 7,825,372 B2 | 11/2010 | Allberg |
| 7,862,534 B2 | 1/2011 | Quirico et al. |
| 7,996,068 B2 | 8/2011 | Telischak et al. |
| 8,058,632 B2 | 11/2011 | Balestracci et al. |
| 8,071,959 B2 | 12/2011 | deKemp |
| 8,198,599 B2 | 6/2012 | Bouton et al. |
| 8,216,181 B2 | 7/2012 | Balestracci |
| 8,216,184 B2 | 7/2012 | Balestracci |
| 8,317,674 B2 | 9/2012 | Quirico et al. |
| 8,295,916 B2 | 10/2012 | Shimchuk et al. |
| 8,431,909 B2 | 4/2013 | Horton et al. |
| 8,439,815 B2 | 5/2013 | Lemer |
| 8,442,803 B2 | 5/2013 | Chen et al. |
| 8,571,881 B2 | 9/2013 | Rousso et al. |
| 8,615,405 B2 | 12/2013 | Rousso et al. |
| 8,708,352 B2 | 4/2014 | Quirico et al. |
| 9,056,164 B2 | 6/2015 | Tate et al. |

(56) References Cited

U.S. PATENT DOCUMENTS

| | | |
|---|---|---|
| 9,056,200 B2 | 6/2015 | Uber, III et al. |
| 9,326,742 B2 | 5/2016 | Hirschman et al. |
| 2002/0128594 A1 | 9/2002 | Das et al. |
| 2002/0129471 A1 | 9/2002 | Wang |
| 2003/0014035 A1 | 1/2003 | Trombley, III et al. |
| 2003/0139640 A1 | 7/2003 | Whittacre et al. |
| 2003/0194894 A1 | 10/2003 | Wariar et al. |
| 2003/0216609 A1 | 11/2003 | Dell et al. |
| 2004/0054319 A1 | 3/2004 | Langley et al. |
| 2004/0104160 A1 | 6/2004 | Scagliarini et al. |
| 2004/0260143 A1 | 12/2004 | Reilly et al. |
| 2005/0029465 A1 | 2/2005 | Lemer |
| 2005/0085682 A1 | 4/2005 | Sasaki et al. |
| 2005/0107698 A1 | 5/2005 | Powers et al. |
| 2005/0187515 A1 | 8/2005 | Varrichio et al. |
| 2005/0277833 A1 | 12/2005 | Williams |
| 2005/0278066 A1 | 12/2005 | Graves et al. |
| 2006/0015056 A1 | 1/2006 | Ellingboe et al. |
| 2006/0151048 A1 | 7/2006 | Tochon-Danguy et al. |
| 2006/0164093 A1 | 7/2006 | Ooe et al. |
| 2006/0173419 A1 | 8/2006 | Malcolm |
| 2006/0235353 A1 | 10/2006 | Gelfand et al. |
| 2007/0080223 A1 | 4/2007 | Japuntich |
| 2007/0140958 A1 | 6/2007 | deKemp |
| 2007/0213848 A1 | 9/2007 | deKemp et al. |
| 2007/0226175 A1 | 9/2007 | Resnic et al. |
| 2007/0232980 A1 | 10/2007 | Felt et al. |
| 2007/0260213 A1 | 11/2007 | Williams et al. |
| 2007/0282263 A1 | 12/2007 | Kalafut et al. |
| 2008/0015794 A1 | 1/2008 | Eiler et al. |
| 2008/0035542 A1 | 2/2008 | Mourtada et al. |
| 2008/0071219 A1 | 3/2008 | Rhinehart et al. |
| 2008/0093564 A1 | 4/2008 | Tartaglia et al. |
| 2008/0128626 A1 | 6/2008 | Rousso et al. |
| 2008/0131362 A1 | 6/2008 | Rousso et al. |
| 2008/0152083 A1 | 6/2008 | Juni |
| 2008/0166292 A1 | 7/2008 | Levin et al. |
| 2008/0177126 A1 | 7/2008 | Tate et al. |
| 2008/0191148 A1 | 8/2008 | Gibson |
| 2008/0195249 A1 | 8/2008 | Rousso et al. |
| 2008/0200747 A1 | 8/2008 | Wagner et al. |
| 2008/0203318 A1 | 8/2008 | Wagner et al. |
| 2008/0224065 A1 | 9/2008 | Pollard Jr. |
| 2008/0237502 A1 | 10/2008 | Fago |
| 2008/0242915 A1 | 10/2008 | Jackson et al. |
| 2008/0260580 A1 | 10/2008 | Helle et al. |
| 2009/0032729 A1 | 2/2009 | Piancastelli |
| 2009/0112478 A1 | 4/2009 | Mueller, Jr. et al. |
| 2009/0155167 A1 | 6/2009 | Powell et al. |
| 2009/0224171 A1 | 9/2009 | Verbokkem |
| 2009/0312630 A1 | 12/2009 | Hidem et al. |
| 2009/0312635 A1 | 12/2009 | Shimchuk et al. |
| 2010/0030009 A1 | 2/2010 | Lemer |
| 2010/0312039 A1 | 12/2010 | Quirico et al. |
| 2011/0071392 A1 | 3/2011 | Quirico et al. |
| 2011/0172524 A1 | 7/2011 | Hidem et al. |
| 2011/0178359 A1 | 7/2011 | Hirschman et al. |
| 2011/0209764 A1 | 9/2011 | Uber et al. |
| 2012/0098671 A1 | 4/2012 | Wieczorek et al. |
| 2012/0305730 A1 | 12/2012 | Balestracci |
| 2012/0310031 A1 | 12/2012 | Quirico et al. |
| 2012/0312980 A1 | 12/2012 | Whitehouse |
| 2013/0300109 A1 | 11/2013 | Balestracci et al. |
| 2014/0084187 A1 | 3/2014 | Quirico et al. |
| 2014/0175959 A1 | 6/2014 | Quirico et al. |
| 2014/0343418 A1 | 11/2014 | Quirico et al. |
| 2014/0374614 A1 | 12/2014 | Hidem et al. |
| 2014/0374615 A1 | 12/2014 | Hidem et al. |
| 2015/0260855 A1 | 9/2015 | McQuaid et al. |

FOREIGN PATENT DOCUMENTS

| | | |
|---|---|---|
| CN | 1137239 A | 12/1996 |
| CN | 1431488 A | 7/2003 |
| CN | 1460849 A | 12/2003 |
| CN | 1471644 A | 1/2004 |
| CN | 2677923 Y | 2/2005 |
| CN | 1946432 A | 4/2007 |
| CN | 1968653 A | 5/2007 |
| CN | 101015459 A | 8/2007 |
| CN | 201017036 Y | 2/2008 |
| CN | 101401009 A | 4/2009 |
| CN | 101801440 A | 8/2010 |
| CN | 104332198 A | 2/2015 |
| CN | 104536031 A | 4/2015 |
| CN | 104597472 A | 5/2015 |
| DE | 19622184 A1 | 12/1997 |
| DE | 19918342 B4 | 5/2017 |
| EP | 102121 A1 | 3/1984 |
| EP | 117752 A2 | 9/1984 |
| EP | 160303 A2 | 11/1985 |
| EP | 310148 A2 | 4/1989 |
| EP | 317114 A1 | 5/1989 |
| EP | 319148 A2 | 6/1989 |
| EP | 919249 A1 | 6/1999 |
| EP | 1421960 A1 | 5/2004 |
| EP | 1772157 A1 | 4/2007 |
| EP | 1820730 A1 | 8/2007 |
| EP | 2332593 A2 | 6/2011 |
| EP | 2011126 B1 | 5/2012 |
| EP | 2492920 A2 | 8/2012 |
| EP | 2542276 A1 | 1/2013 |
| EP | 2896049 A1 | 7/2015 |
| FR | 2867084 A1 | 9/2005 |
| JP | 2000350783 A | 12/2000 |
| JP | 3137622 B1 | 2/2001 |
| JP | 2003520780 A | 7/2003 |
| JP | 2006017660 A | 1/2006 |
| JP | 2006043212 A | 2/2006 |
| JP | 2006325826 A | 12/2006 |
| JP | 2008023346 A | 2/2008 |
| JP | 2011161262 A | 8/2011 |
| KR | 960003726 B1 | 3/1996 |
| KR | 20150125046 A | 11/2015 |
| RU | 2131273 C1 | 6/1999 |
| RU | 2288755 C1 | 12/2006 |
| RU | 65383 U1 | 8/2007 |
| RU | 2429886 C2 | 9/2011 |
| RU | 2575309 C2 | 2/2016 |
| RU | 2599866 C2 | 10/2016 |
| RU | 2606169 C2 | 1/2017 |
| SU | 244513 A1 | 12/1969 |
| TW | 391868 B | 6/2000 |
| WO | 9615337 A1 | 5/1996 |
| WO | 9956117 A1 | 11/1999 |
| WO | 0156634 A1 | 8/2001 |
| WO | 02096335 A2 | 12/2002 |
| WO | 03034444 A1 | 4/2003 |
| WO | 2004004787 A2 | 1/2004 |
| WO | 2004059661 A1 | 7/2004 |
| WO | 2004080523 A2 | 9/2004 |
| WO | 2005002971 A1 | 1/2005 |
| WO | 2006007750 A1 | 1/2006 |
| WO | 2006026603 A2 | 3/2006 |
| WO | 2006074473 A2 | 7/2006 |
| WO | 2006129301 A2 | 12/2006 |
| WO | 2006135374 A2 | 12/2006 |
| WO | 2007016170 A1 | 2/2007 |
| WO | 2007016173 A1 | 2/2007 |
| WO | 2007030249 A2 | 3/2007 |
| WO | 2007041017 A1 | 4/2007 |
| WO | 2007071022 A1 | 6/2007 |
| WO | 2007082093 A2 | 7/2007 |
| WO | 2007096119 A2 | 8/2007 |
| WO | 2007104133 A1 | 9/2007 |
| WO | 2007149108 A2 | 12/2007 |
| WO | 2008028165 A2 | 3/2008 |
| WO | 2008037939 A2 | 4/2008 |
| WO | 2008066586 A2 | 6/2008 |
| WO | 2008082966 A2 | 7/2008 |
| WO | 2008140351 A1 | 11/2008 |
| WO | 2009152320 A2 | 12/2009 |
| WO | 2009152323 A2 | 12/2009 |
| WO | 2010020596 A1 | 2/2010 |

(56) References Cited

FOREIGN PATENT DOCUMENTS

| WO | 2011126522 A2 | 10/2011 |
|---|---|---|
| WO | 2013082699 A1 | 6/2013 |
| WO | 2013085428 A1 | 6/2013 |
| WO | 2014036627 A1 | 3/2014 |
| WO | 2018057634 A1 | 3/2018 |
| WO | 2018057635 A1 | 3/2018 |
| WO | 2018057636 A1 | 3/2018 |
| WO | 2019191384 A1 | 10/2019 |

OTHER PUBLICATIONS 337-1110_662795: Staff's Response to Respondents' Motion for Summary Determination of Noninfringement of U.S. Pat. Nos. 9,750,869; 9,750,870; and 9,814,826 by Respondents' Version 3.1 and 4 Designs (Motion Response/Reply); 1-1389338: "Staff's Response to Respondents' Motion for Summary Determination of Noninfringement of U.S. Pat. Nos. 9,750,869; 9,750,870; and 9,814,826 by Respondents' Version 3.1 and 4 Designs", create date Nov. 28, 2018, www edis.usitc.gov.
337-1110_662796: Staff's Response to Complainant's Motion for Summary Determination of Infringement and Satisfaction of the Economic & Technical Prongs of the Domestic Industry Requirement (Motion Response/Reply); 1-1389340: "Staff's Response to Complainant's Motion for Summary Determination of Infringement & Satisfaction of the Economic & Technical Prongs of the Domestic Industry Requirement", create date Nov. 28, 2018, www.edis.usitc.gov.
Attachment D: Respondents' Obviousness Contentions, Exchanged in ITC Investigation No. 337-TA-1110, Aug. 8, 2018, 38 pages (Confidential Business Information Redacted).
Exhibit D.1: U.S. Pat. No. 9,814,826 Claim Chart—Obviousness Over Klein, Exchanged in ITC Investigation No. 337-TA-1110, Aug. 8, 2018, 207 pages. (Confidential Business Information Redacted).
Exhibit D.2: U.S. Pat. No. 9,750,869 Claim Chart—Obviousness Over Klein, Exchanged in ITC Investigation No. 337-TA-1110, Aug. 8, 2018, 244 pages. (Confidential Business Information Redacted).
Exhibit D.3: U.S. Pat. No. 9,750,870 Claim Chart—Obviousness Over Klein, Exchanged in ITC Investigation No. 337-TA-1110, Aug. 8, 2018, 172 pages. (Confidential Business Information Redacted).
Exhibit D.4: U.S. Pat. No. 9,814,826 Claim Chart—Obviousness Over Cardiogen-82, Exchanged in ITC Investigation No. 337-TA-1110, Aug. 8, 2018, 224 pages. (Confidential Business Information Redacted).
Exhibit D.5: U.S. Pat. No. 9,750,869 Claim Chart—Obviousness Over Cardiogen-82, Exchanged in ITC Investigation No. 337-TA-1110, Aug. 8, 2018, 255 pages. (Confidential Business Information Redacted).
Exhibit D.6: U.S. Pat. No. 9,750,870 Claim Chart—Obviousness Over Cardiogen-82, Exchanged in ITC Investigation No. 337-TA-1110, Aug. 8, 2018, 199 pages. (Confidential Business Information Redacted).
Bracco Diagnostics Inc.'s Rebuttal Contentions in Response to Respondents' Aug. 8, 2018 Contentions (Including Responses to OUII Staff ROG Nos. 13, 18, 19, 20-22, 32 and Respondents' ROG Nos. 5, 9-11, 18, 33), Investigation No. 337-TA-1110, Aug. 15, 2018, 35 pages. (Confidential Business Information Redacted).
Supplemental Exhibit 1, Response to Supplemental Exhibit D.1: U.S. Pat. No. 9,814,826 Invalidity Contentions, Exchanged in ITC Investigation No. 337-TA-1110, Aug. 15, 2018, 22 pages. (Confidential Business Information Redacted).
Supplemental Exhibit 2, Response to Supplemental Exhibit D.2: U.S. Pat. No. 9,750,869 Invalidity Contentions, Exchanged in ITC Investigation No. 337-TA-1110, Aug. 15, 2018, 23 pages. (Confidential Business Information Redacted).
Supplemental Exhibit 3, Complainant's Supplemental Response to Respondents' Supplemental Exhibit D.3: U.S. Pat. No. 9,750,870 Invalidity Contentions, Exchanged in ITC Investigation No. 337-TA-1110, Aug. 15, 2018, 19 pages. (Confidential Business Information Redacted).
Bracco Diagnostics Inc.'s Supplemental Rebuttal Contentions in Response to Respondents' Aug. 8, 2018 Contentions Pursuant to Order No. 16, Investigation No. 337-TA-1110, Aug. 23, 2018, 18 pages. (Confidential Business Information Redacted).
Supplemental Exhibit 1, Response to Supplemental Exhibit D.1: U.S. Pat. No. 9,814,826 Invalidity Contentions, Exchanged in ITC Investigation No. 337-TA-1110, Aug. 23, 2018, 22 pages. (Confidential Business Information Redacted).
Supplemental Exhibit 2, Response to Supplemental Exhibit D.2: U.S. Pat. No. 9,750,869 Invalidity Contentions, Exchanged in ITC Investigation No. 337-TA-1110, Aug. 23, 2018, 25 pages. (Confidential Business Information Redacted).
Supplemental Exhibit 3, Complainant's Supplemental Response to Respondents' Supplemental Exhibit D.3: U.S. Pat. No 9,750,870 Invalidity Contentions, Aug. 23, 2018, 26 pages. (Confidential Business Information Redacted).
Exhibit 4, Response to Exhibit D.4: U.S. Pat. No. 9,814,826 Invalidity Contentions, Aug. 23, 2018, 37 pages. (Confidential Business Information Redacted).
Exhibit 5, Response to Exhibit D.5: U.S. Pat. No. 9,814,826 Invalidity Contentions, Aug. 23, 2018, 39 pages. (Confidential Business Information Redacted).
Supplemental Exhibit 6, Complainant's Supplemental Response to Respondents' Supplemental Exhibit D.6: U.S. Pat. No. 9,750,870 Invalidity Contentions, Aug. 23, 2018, 44 pages (Confidential Business Information Redacted).
337-1110_652068: Respondents' Jubilant DraxImage Inc., Jubilant Pharma Limited, and Jubilant Life Sciences Limited Notice of Prior Art (Notice of Prior Art); 1-1311880: "Respondents First Supplemental Notice of Prior Art", create date Aug. 3, 2018, www.edis.usitc.gov, 29 pages.
Respondents' Pre-Hearing Brief, Public Version, Investigation No. 337-TA-1110, Dec. 12, 2018, 550 pages.
Complainant Bracco Diagnostics Inc.'s Pre-Hearing Brief, Public Version, Inv. No. 337-TA-1110, Dec. 13, 2018, 568 pages.
Report of Robert T. Stone, Ph.D on Invalidity of U.S. Pat. No. 9,750,869, 9,750,870 and 9,814,826, Sep. 17, 2018, 1051 pages. (Confidential Business Information Redacted).
Corrected Expert Report of Norbert J. Pelc, Sc.D, Investigation No. 337-TA-1110, Oct. 1, 2018, 289 pages. (Confidential Business Information Redacted).
Declaration of Robert T. Stone, Ph.D., *Jubilant DraxImage Inc. v. Bracco Diagnostics Inc.*, IPR2018-01448 and IPR2018-01450, Exhibit 1015, Aug. 17, 2018, 267 pages.
Curriculum Vitae of Robert T. Stone, Ph.D., *Jubilant DraxImage Inc. v. Bracco Diagnostics Inc.*, IPR2018-01448, Exhibit 1016, filed Aug. 22, 2018, 10 pages.
Declaration of Venkatesh L. Murthy, M.D., Ph.D., *Jubilant DraxImage Inc. v. Bracco Diagnostics Inc.*, IPR2018-01448, Exhibit 1017, Aug. 14, 2018, 52 pages.
US Pharmacopeia 23 National Formulary 18, 1995, 5 pages (cited as Exhibit 1019 in IPR2018-01448, *Jubilant DraxImage Inc. v. Bracco Diagnostics Inc.*).
Declaration of Andy Adler, Ph.D., *Jubilant DraxImage Inc. v. Bracco Diagnostics Inc.*, IPR2018-01448, Exhibit 1020, Aug. 17, 2018, 156 pages.
Bracco CardioGen-82 Infusion System User's Guide, Rev. 07, Jul. 20, 2004, 49 pages (cited as Exhibit 1021 in IPR2018-01448, *Jubilant DraxImage Inc. v. Bracco Diagnostics Inc.*).
Chatal et al., "Story of rubidium-82 and advantages for myocardial perfusion PET imaging," Frontiers in Medicine, v. 2, art. 65, Sep. 11, 2015, pp. 1-7 (cited as Exhibit 1026 in IPR2018-01448, *Jubilant DraxImage Inc. v. Bracco Diagnostics Inc.*).
ISO 13485:2003—Medical Devices—Quality Management Systems—Requirements for Regulatory Purposes, Jul. 15, 2003, 64 pages (cited as Exhibit 1028 in IPR2018-01448, Jubilant Draximage Inc v. Bracco Diagnostics Inc ).
21 CFR Part 820.1, US Food and Drug Administration, HHS, 2005, pp. 152-153 (cited as Exhibit 1029 in IPR2018-01448, *Jubilant DraxImage Inc. v. Bracco Diagnostics Inc.*).

(56) References Cited

OTHER PUBLICATIONS

EN 62274:2005—Medical Electrical Equipment—Safety of Radiotherapy Record and Verify Systems, Dec. 28, 2005, 22 pages (cited as Exhibit 1030 in IPR2018-01448, *Jubilant DraxImage Inc. v. Bracco Diagnostics Inc.*).
21 CFR Part 11.1, US Food and Drug Administration, HHS, 2004, pp. 109-110 (cited as Exhibit 1031 in IPR2018-01448, *Jubilant DraxImage Inc. v. Bracco Diagnostics Inc.*).
10 CFR Part 20.1001-1002, Nuclear Regulatory Commission, 2005, pp. 317-318 (cited as Exhibit 1032 in IPR2018-01448, *Jubilant DraxImage Inc. v. Bracco Diagnostics Inc.*).
10 CFR Part 20.1003, Nuclear Regulatory Commission, 2005, pp. 318-324 (cited as Exhibit 1033 in IPR2018-01448, *Jubilant DraxImage Inc. v. Bracco Diagnostics Inc.*).
Wang et al., Handbook of Radioactive Nuclides, The Chemical Rubber Co., 1969, 59 pages (cited as Exhibit 1034 in IPR2018-01448, *Jubilant DraxImage Inc. v. Bracco Diagnostics Inc.*).
Bates et al., "Effect of Computerized Physician Order Entry and a Team Intervention on Prevention of Serious Medication Errors," JAMA, vol. 280, No. 15, Oct. 21, 1998, pp. 1311-1316 (cited as Exhibit 1035 in IPR2018-01448, *Jubilant DraxImage Inc. v. Bracco Diagnostics Inc.*).
Bates et al., "The Impact of Computerized Physician Order Entry on Medication Error Prevention," Journal of the American Medical Informatics Association, vol. 6, No. 4, Jul./Aug. 1999, pp. 313-321 (cited as Exhibit 1036 in IPR2018-01448, *Jubilant DraxImage Inc. v. Bracco Diagnostics Inc.*).
Medical Devices Security Technical Implementation Guide, Defense Information Systems Agency, Version 1, Release 1, Jul. 27, 2010, 56 pages (cited as Exhibit 1037 in IPR2018-01448, *Jubilant DraxImage Inc. v. Bracco Diagnostics Inc.*).
Implementation Guide for the Use of Bar Code Technology in Healthcare, HIMSS, 2003, 72 pages (cited as Exhibit 1038 in IPR2018-01448, *Jubilant DraxImage Inc. v. Bracco Diagnostics Inc.*).
337-TA-1110: Complainant Bracco Diagnostics Inc.'s Responses to Respondents Jubilant DraxImage, Inc.'s, Jubilant Pharma Limited's, and Jubilant Life Sciences' Fourth Set of Interrogatories (No. 68), Aug. 6, 2018, 11 pages (cited as Exhibit 1039 in IPR2018-01448, *Jubilant DraxImage Inc. v. Bracco Diagnostics Inc.*).
Declaration of Carol Wadke, *Jubilant DraxImage Inc. v. Bracco Diagnostics Inc.*, IPR2018-01448, Exhibit 1042, Jul. 27, 2018, 174 pages.
Petition for Inter Partes Review of U.S. Pat. No. 9,299,468, *Jubilant DraxImage Inc. v. Bracco Diagnostics Inc.*, IPR2018-01448, Aug. 22, 2018, 97 pages.
Patent Owner's Submission of Mandatory Notice Information Under 37 CFR 42.8(a)(2), *Jubilant DraxImage Inc. v. Bracco Diagnostics Inc.*, IPR2018-01448, Sep. 13, 2018, 4 pages.
Patent Owner's Preliminary Response, *Jubilant DraxImage Inc. v. Bracco Diagnostics Inc.*, IPR2018-01448, Nov. 29, 2018, 79 pages.
Redline comparison between US Patent Publication No. 2004/0260143 A1 (Reilly et al.), published Dec. 23, 2004 and U.S. Pat. No. 6,767,319 B2 (Reilly et al.), issued Jul. 27, 2004, filed Nov. 29, 2018 as Exhibit 2002 in IPR2018-01448, *Jubilant DraxImage Inc. v. Bracco Diagnostics Inc.*, 22 pages.
"Alaris GH Syringe Pump Directions For Use," Cardinal Health, Oct. 2005, 34 pages.
Alvarez-Diez et al. "Manufacture of strontium-82/rubidium-82 generators and quality control of rubidium-82 chloride for myocardial perfusion imaging in patients using positron emission tomography," Applied Radiation and Isotopes, 1999, pp. 1015-1023.
"Auto Syringe AS40A: Model AS40A Infusion Pump Operation Manual," Baxter, Aug. 1993, 84 pages.
"BodyGuard 323 Infusion Pump System Operator Manual," Caesarea Medical Electronics Ltd, Mar. 2009, 81 pages.
Brochure, "IV and Liquid Filters: Speedflow Adult 0.2 um Positive", http://www.gvs.it/flex/FixedPages/UK/LiquidFilters.php/L/UK/ID/Speedflow%20Adjust% . . . Retrieved from URL on Nov. 11, 2008.
Bracco Brochure, "Rubidium 82 Infusion System, Easy to Operate . . . Automated . . . Complete", © Bracco Diagnostics, Inc., 0605-002NA, Jun. 2001, (2 pages).
"CardioGen-82 Infusion System User's Guide," Medical Product Service GmbH, Jul. 3, 2007, 53 pages.
"CardioGen-82 Rubidium Rb 82 Generator For Elution of Rubidium Chloride Rb 82 Injection," Bracco Diagnostics, May 2000, 13 pages.
Daraban et al., "Efficiency Calibration in Gamma Spectrometry by Using 232Th Series Radionuclides," Romanian Journal of Physics, vol. 58, Supplement, 2013, pp. S99-S107.
Neil J. Epstein, "A Rb82 infusion system for quantitative perfusion imaging with 3D PET" Applied Radiation and Isotopes, vol. 60, Feb. 9, 2004, pp. 921-927, XP002557544 DOI:10, 1016/j. apradiso. 2004.02.002.
International Patent Application No. PCT/US2019/024515, International Search Report and Written Opinion dated Jun. 24, 2019, 13 pages.
Imaging Technology News, web exclusive: "FDG-PET Injector Thrusts New Life into Molecular Imaging", Apr. 2008, 2 pages.
R. Klein, "Precise 82RB infusion system for cardiac perfusion measurement using 3D positron emission tomography", Ottawa-Carleton Institute for Electrical and Computer Engineering School of Information Technology and Engineering Electrical & Computer Engineering), Feb. 2005, 147 pages.
R. Klein, "Precision control of eluted Activity from a Sr/Rb generator for cardiac positron emission tomography", Proceedings of the 26th Annual International Conference of the IEEE EMBS San Francisco, CA, USA, Sep. 1-5, 2004, 4 pages.
R. Klein, "Precision controlled elution of a Sr82/Rb82 generator for cardiac perfusion imaging with positron emission tomography" Physics in Medicine and Biology, vol. 52, Jan. 11, 2007, pp. 659-673, XP002557545 DOI: 10, 1088/0031-9155/52/3/009.
Kost, "Preventing Medical Errors in Point-of-Care Testing," Archives of Pathology & Laboratory Medicine, vol. 125, No. 10, Oct. 2001, pp. 1307-1315.
Lemer Pax, POSIJET® Integrated FDG dispensing and infusion system, www.lemerpax.com (copyright date May 2008).
Leveson, "Medical Devices: The Therac-25*," Appendix of: Safeware: System Safety and Computers, 1995, 49 pages.
Lortie et al., "Quantification of myocardial blood flow with 82Rb dynamic PET imaging," Eur. J. Nucl. Med. Mol. Imaging, vol. 34, 2007, pp. 1765-1774.
Luca et al., "Calibration of the High and Low Resolution Gamma-Ray Spectrometers," Romanian Reports in Physics, vol. 64, No. 4, 2012, pp. 968-976.
Machine translation of abstract of RU2307378 published Sep. 27, 2007 (Oao Sojuztsvetmetavtomatika).
"Medfusion 3000 Series Technical Service Manual," Smiths Medical, 2010, 184 pages.
Neirincks et al., "Evaluation of Inorganic Adsorbents for the Rubidium-82 Generator: I. Hydrous SnO2," The Journal of Nuclear Medicine, vol. 23, No. 3, Jan. 1, 1982, pp. 245-249.
Rawool-Sullivan et al., "Use of Wavelet Denoising in Identifying Radioactive Isotopes Using a Gamma-Ray Spectrum," Summary #2826 American Nuclear Society, Winter 2010 conference, Nov. 1, 2010, 4 pages.
337-1110_640015: Public Version of Complaint and Exhibits 1-28 (Complaint); 1-1283977: "640015 Public Complaint: GreenbergTraurig's letter dated Mar. 27, 2018 re Complainant's filing of documents to support Bracco's request that the Commission commence 337 investigation", create date Apr. 13, 2018, www.edis.usitc.gov.
337-1110_643191: Notice of Institution of Investigation (Notice); 1-1285952: "1285952: Notice of Institution of Investigation Inv. No. 337-TA-1110", create date Apr. 25, 2018, www.edis.usitc.gov.
337-1110_647318: Joint List of Disputed and Undisputed Claim Terms (Other); 1-1298795: "1298795: Joint List of Disputed and Undisputed Claim Terms", create date Jun. 8, 2018, www.edis.usitc.gov.
337-1110_648102: Proposed Construction of Disputed Claim Terms (Response/Submission to ALJ Order); 1-1301950: "Proposed Constructions", create date Jun. 18, 2018, www.edis.usitc.gov.

(56) References Cited

OTHER PUBLICATIONS 337-1110_650007: Respondent Jubilant DraxImage Inc., Jubilant Pharma Limited, and Jubilant Life Sciences Limited's Notice of Prior Art (Notice of Prior Art); 1-1306444: "Notice of Prior Art", create date Jul. 10, 2018, www.edis.usitc.gov.
337-1110_652080: Joint Unopposed Motion for Leave to File Joint Submission of Identification of Claim Terms and Proposed Constructions Thereof out of Time (Motion); 2-1311910: "Identification of Claim Terms", create date Aug. 3, 2018, www.edis.usitc.gov. create date Aug. 3, 2018, www.edis.usitc.gov.
337-1110_652479: Granting Joint Motion to File Identification of Claim Terms and Constructions out of Time (Order); 1-1313857: "652479: Order No. 14", create date Aug. 8, 2018, www.edis.usitc.gov.
337-1110_661785: Complainant Bracco Diagnostics Inc.'s Motion for Summary Determination of Infringement and Satisfaction of the Economic and Technical Prongs of the Domestic Industry Requirement (Motion); 1-1385894: "Letter to Barton", create date Nov. 14, 2018, www.edis.usitc.gov.
337-1110_661785: Complainant Bracco Diagnostics Inc.'s Motion for Summary Determination of Infringement and Satisfaction of the Economic and Technical Prongs of the Domestic Industry Requirement (Motion); 2-1385895: "Motion for Summary Determination", create date Nov. 14, 2018, www.edis.usitc.gov.
337-1110_661785: Complainant Bracco Diagnostics Inc.'s Motion for Summary Determination of Infringement and Satisfaction of the Economic and Technical Prongs of the Domestic Industry Requirement (Motion); 3-1385896: "Chart of Undisputed Material Facts", create date Nov. 14, 2018, www.edis.usitc.gov.
337-1110_661851: Errata to Staff's Response to Complainant's Motion for Summary Determination of Infringement and Satisfaction of the Economic and Technical Prongs of the Domestic Industry Requirement (Motion Response/Reply); 1-1385993:, create date Nov. 14, 2018, www.edis.usitc.gov.
337-1110_660985: Respondents' Motion for Summary Determination of Noninfringement of U.S. Pat. Nos. 9,750,869, 9,750,870, and 9,814,826 by Respondents' Version 3.1 and Version 4 Designs (Motion); 1-1383714: "Respondents' Motion for Summary Determination (PV)", create date Nov. 5, 2018, www.edis.usitc.gov.
337-1110_660985: Respondents' Motion for Summary Determination of Noninfringement of U.S. Pat. Nos. 9,750,869, 9,750,870, and 9,814,826 by Respondents' Version 3.1 and Version 4 Designs (Motion); 2-1383715: "Memorandum in Support of Respondents' Motion for Summary Determination (PV)", create date Nov. 5, 2018, www.edis.usitc.gov.
337-1110_660985: Respondents' Motion for Summary Determination of Noninfringement of U.S. Pat. Nos. 9,750,869, 9,750,870, and 9,814,826 by Respondents' Version 3.1 and Version 4 Designs (Motion); 17-1383730: "Chart of Material Facts in Support of Respondents' MSD", create date Nov. 5, 2018, www.edis.usitc.gov.
337-1110_661010: Complainant Bracco Diagnostics Inc.'s Motion for Summary Determination of Infringement and Satisfaction of the Economic and Technical Prongs of the Domestic Industry Requirement (Motion); 1-1383879 "Bracco's Motion for Summary Determination", create date Nov. 5, 2018, www.edis.usitc.gov.
337-1110_661010: Complainant Bracco Diagnostics Inc.'s Motion for Summary Determination of Infringement and Satisfaction of the Economic and Technical Prongs of the Domestic Industry Requirement (Motion); 2-1383880 "Bracco's Chart of Undisputed Material Facts", create date Nov. 5, 2018, www.edis.usitc.gov.
337-1110_661038: Respondents' Unopposed Motion to Replace Respondents' Chart of Material Facts in Support of Motion for Summary Determination (Motion); 1-1383923: "Respondents' Unopposed Motion to Replace Respondents' Chart of Material Facts in Support of Motion for Summary Determination (Public Version)", create date Nov. 5, 2018, www.edis.usitc.gov.
337-1110_662007: Respondents' Memorandum in Opposition of Complainant's Motion for Summary Determination of Infringement and Satisfaction of the Economic and Technical Prongs of the Domestic Industry Requirement (Motion Response/Reply); 1-1386474:

"Respondents' Memorandum in Opposition to Complainant's Motion for Summary Determination (PV)", create date Nov. 16, 2018, www.edis.usitc.gov.
Ruby Rubidium Elution System User Manual, Jubilant DraxImage, Version 7, Created Jun. 3, 2014, Modified Jan. 9, 2015, 58 pages.
Intego PET Infusion System Operation Manual, Medrad, Rev. G, Jun. 2013, 142 pages.
Commission Investigative Staff's Prehearing Brief, Inv. No. 337-TA-1110, Dec. 20, 2018, 129 pages. (Confidential Business Information Redacted).
Saha et al., "Use of the 82Sr/82Rb Generator in Clinical PET Studies*," International Journal of Radiation Applications and Instrumentation, Part B. Nuclear Medicine and Biology, vol. 17, No. 8, 1990, pp. 763-768.
Yano et al., "Evaluation and Application of Alumina-Based Rb-82 Generators Charged with High Levels of Sr-82/85," The Journal of Nuclear Medicine, vol. 20, No. 9, 1979, pp. 961-966.
Yano et al., "A Precision Flow-Controlled Rb-82 Generator for Bolus or Constant-Infusion Studies of the Heart and Brain," The Journal of Nuclear Medicine, Preliminary Notes, vol. 22, No. 11, 1981, pp. 1006-1010.
Yano, "Essentials of a Rubidium-82 Generator for Nuclear Medicine," International Journal of Radiation Applications and Instrumentation, Part A. Applied Radiation and Isotopes, vol. 38, No. 3, 1987, pp. 205-211.
337-1110_662084: Complainant Bracco Diagnostics Inc.'s Response to Jubilant's Motion for Summary Determination of Noninfringement of U.S. Pat. Nos. 9,750,869, 9,750,870, and 9,814,826 by Jubilant's Version 3.1 and Version 4 Designs and Memorandum in Support Thereof (Motion Response/Reply); 1-1386969: "Complainant's Response to Motion for Summary Determination", create date Nov. 19, 2018, www.edis.usitc.gov.
Declaration of Robert T. Stone, Ph.D., *Jubilant DraxImage Inc. v. Bracco Diagnostics Inc.*, IPR2018-01449, Exhibit 1015, Aug. 16, 2018, 175 pages.
Petition for Inter Partes Review of U.S. Pat. No. 9,299,467, *Jubilant DraxImage Inc. v. Bracco Diagnostics Inc.*, IPR2018-01449, Aug. 22, 2018, 77 pages.
Patent Owner's Submission of Mandatory Notice Information Under 37 CFR 42.8(a)(2), *Jubilant DraxImage Inc. v. Bracco Diagnostics Inc.*, IPR2018-01449, Sep. 13, 2018, 4 pages.
Patent Owner's Preliminary Response, *Jubilant DraxImage Inc. v. Bracco Diagnostics Inc.*, IPR2018-01449, Nov. 29, 2018, 75 pages.
Petition for Inter Partes Review of U.S. Pat. No. 9,299,468, *Jubilant DraxImage Inc. v. Bracco Diagnostics Inc.*, IPR2018-01450, Aug. 22, 2018, 56 pages.
Patent Owner's Submission of Mandatory Notice Information Under 37 CFR 42.8(a)(2), *Jubilant DraxImage Inc. v. Bracco Diagnostics Inc.*, IPR2018-01450, Sep. 13, 2018, 4 pages.
Patent Owner's Preliminary Response, *Jubilant DraxImage Inc. v. Bracco Diagnostics Inc.*, IPR2018-01450, Nov. 30, 2018, 64 pages.
Decision to Institute in IPR2018-01448, U.S. Pat. No. 9,299,468 B2, *Jubilant DraxImage Inc. v. Bracco Diagnostics Inc.*, Feb. 8, 2019, 22 pages.
Decision to Institute in IPR2018-01449, U.S. Pat. No. 9,299,467 B2, *Jubilant DraxImage Inc. v. Bracco Diagnostics Inc.*, Feb. 8, 2019, 21 pages.
Decision to Institute in IPR2018-01450, U.S. Pat. No. 9,299,468 B2, *Jubilant DraxImage Inc. v. Bracco Diagnostics Inc.*, Feb. 8, 2019, 19 pages.
ELFO Automatic Radiopharmaceutical Injection System for PET Imaging, Date Not Identified, 3 pages.
Commission Opinion, Inv. No. 337-TA-1110, Public Version, Dec. 11, 2019, 43 pages.
Bracco Diagnostics Inc.'s Petition for Review with Exhibits 1, 2 and 3, Inv. No. 337-TA-1110, Dec. 23, 2019, 240 pages.
Initial Determination on Violation of Section 337 and Recommended Determination on Remedy and Bond, Inv. No. 337-TA-1110, Public Version, Aug. 1, 2019, 185 pages.
Final Written Decision in IPR2018-01448, U.S. Pat. No. 9,299,468 B2, *Jubilant DraxImage Inc. v. Bracco Diagnostics Inc.*, Feb. 6, 2020, 98 pages.

(56) References Cited

OTHER PUBLICATIONS

Final Written Decision in IPR2018-01449, U.S. Pat. No. 9,299,467 B2, *Jubilant DraxImage Inc.* v. *Bracco Diagnostics Inc.*, Feb. 6, 2020, 58 pages.
Final Written Decision in IPR2018-01450, U.S. Pat. No. 9,299,468 B2, *Jubilant DraxImage Inc.* v. *Bracco Diagnostics Inc.*, Feb. 6, 2020, 51 pages.
Nunn, U.S. Appl. No. 62/979,886, filed Feb. 21, 2020, entitled Radioisotope Generator Early Breakthrough Detection, 51 pages.

EARLY DETECTION OF RADIOISOTOPE GENERATOR END LIFE

CROSS-REFERENCE

This application is a 35 U.S.C. 371 national phase filing from International Application No. PCT/US2019/024515, filed Mar. 28, 2019, which claims the benefit of U.S. Provisional Patent Application No. 62/649,556, filed Mar. 28, 2018. The entire contents of each application are incorporated herein by reference.

TECHNICAL FIELD

This disclosure relates to radiopharmaceuticals used in nuclear medicine and, more particularly, to systems and techniques monitoring and/or controlling radiopharmaceutical delivery systems.

BACKGROUND

Nuclear medicine employs radioactive material for therapy and diagnostic imaging. Positron emission tomography (PET) is one type of diagnostic imaging, which utilizes doses of radiopharmaceutical. The doses of radiopharmaceutical may be injected or infused into a patient prior to or during a PET scan procedure. An infused dose of radiopharmaceutical can be absorbed by cells of a target organ of the patient and emit radiation. A PET scanner can detect the emitted radiation in order to generate image of an organ. For example, to image body tissue such as the myocardium, a patient may be injected or infused with rubidium-82 ($^{82}$Rb). Rubidium-82 may exhibit similar physiological uptake as potassium and, accordingly, may be taken into the myocardium following potassium pathways.

Rubidium-82 can be generated for nuclear medicine procedures using a strontium-rubidium generator ($^{82}$Sr/$^{82}$Rb generator). Rubidium-82 is a radioactive decay product of strontium-82. Typically, strontium-rubidium generators contain strontium bound to a generator column through which an eluant is flushed during operation. As strontium-82 decays to rubidium-82, the rubidium-82 may release from the generator column and enter the eluant. The resulting stream, which is called an eluate, can be injected or infused into a patient.

SUMMARY

In general, this disclosure is directed to systems and techniques for predicting when a radioisotope generator used in a radiopharmaceutical delivery system will reach a replacement time in its service life. The replacement time may correspond to when a certain amount of eluant has passed through the radioisotope generator to generate radioactive eluate. As the radioisotope generator ages and progressively more volume of eluant passes through the radioisotope generator, a concentration of one or more radioisotopes not intended to enter the eluate may, in fact, enter the eluate. The concentration or activity level of these one or more undesired radioisotopes may increase to a level at which it is no longer desirable to inject the eluate into a patient, establishing a replacement time when the radioisotope generator may be replaced.

In practice, for example, a radioactive eluate containing a daughter radioisotope can be generated by passing the eluant across a substrate containing bound parent radioisotope. As the parent radioisotope decays into the daughter radioisotope, the daughter radioisotope may release from the substrate, causing the daughter radioisotope to release into the flowing eluant and thereby generating an eluate via elution. As the radioisotope generator approaches the end of its service life, the parent radioisotope may itself begin releasing from the substrate to which the parent radioisotope is bound, causing the parent radioisotope to release into the flowing eluate produced by the generator in addition to its decay product. The amount of parent radioisotope allowed to enter the eluate may be kept comparatively low. This is because the parent radioisotope may have a much longer half-life than the half-life of the daughter radioisotope and, if injected into the patient, will produce radioactive emissions inside of the patient for a longer period of time than the daughter. For example, in the case of a strontium-rubidium radioisotope generator, the parent strontium-82 radioisotope has a half-life of approximately 25.5 days whereas the half-life of the daughter rubidium-82 radioisotope is approximately 76 seconds.

Operators of current radiopharmaceutical delivery systems can perform a periodic quality control check to determine if the eluate produced by the system has an undesired radioisotope above an acceptable level. The operator may generate a sample of eluate, transfer the sample to a dose calibrator, and then measure the activity of parent radioisotope (and/or other contaminant radioisotope) in the eluate. If the undesired radioisotope is above an acceptable level, the operate may take the radiopharmaceutical delivery system out of service until the radioisotope generator in the system can be refreshed and/or replaced with a new generator that produces eluate of acceptable quality. The unplanned removal of the radiopharmaceutical delivery system from service because of eluate quality control test results can have a number of operational impacts. For example, patient procedures scheduled using the radiopharmaceutical delivery system may need to be rescheduled or otherwise accommodated. Further, because an amount of time may need to pass between when the radiopharmaceutical delivery system is taken out of service and when the radioisotope generator can be replaced, the system may need to remain out of service for some time.

In accordance with some examples of the present disclosure, a radioisotope generator system is described that can proactively and predicatively determine when the system will need to be taken out of service for replacement of the radioisotope generator. For example, the system may track a cumulative volume of radioactive eluate generated by the radioisotope generator and also track an activity of a radioisotope in the radioactive eluate generated by the radioisotope generator, such as a parent radioisotope bound in the radioisotope generator. The system may correlate the tracked volume of radioactive eluate to the tracked activity of the radioisotope to develop a trend between the volume and activity. The system may further extrapolate the developed trend to determine the predicted volume of eluate at which the activity of the radioisotope being tracked is expected to equal and/or exceed a threshold. The operator and/or supplier of the system may respond to the predicted volume determined by the system by scheduling service on the radioisotope generator system or otherwise having a replacement radioisotope generator available for a time when the system is scheduled to reach the predicted volume. This can minimize operational downtime for the system. Further by controlling the system using the predicted behavior to determine when a contaminant radioisotope in the eluate may reach an acceptable limit, the likelihood that the contaminant radioisotope may bypass quality control procedures and enter the eluate at an undetected level may be reduced.

In one example, an infusion system is described that includes a radioisotope generator, an activity detector, and a controller. The radioisotope generator generates a radioactive eluate via an elution. The activity detector is configured to measure an activity of a first radioisotope in the radioactive eluate generated by the radioisotope generator. The controller is configured to track a cumulative volume of radioactive eluate generated by the radioisotope generator and also track the activity of the first radioisotope in the radioactive eluate generated by the radioisotope generator. The controller is further configured to determine a predicted volume of the radioactive eluate generated by the radioisotope generator at which the activity of the first radioisotope in the radioactive eluate will reach a threshold based on the tracked cumulative volume of the radioactive eluate and the tracked activity of the first radioisotope.

In another example, a method is described that includes pumping an eluant through a radioisotope generator of an infusion system and thereby generating a radioactive eluate via elution and measuring an activity of a first radioisotope in the radioactive eluate generated by the radioisotope generator with an activity detector. The method also includes tracking, with one or more processors, a cumulative volume of radioactive eluate generated by the radioisotope generator and tracking, with one or more processors, the activity of the first radioisotope in the radioactive eluate generated by the radioisotope generator. The method also includes determining, with the one or more processors, a predicted volume of the radioactive eluate generated by the radioisotope generator at which the activity of the first radioisotope in the radioactive eluate will reach a threshold based on the tracked cumulative volume of the radioactive eluate and the tracked activity of the first radioisotope.

The details of one or more examples are set forth in the accompanying drawings and the description below. Other features, objects, and advantages will be apparent from the description and drawings, and from the claims.

DETAILED DESCRIPTION

In general, the disclosure relates to real time detection and quantification of different radioisotopes in a sample. The described systems and techniques can be implemented to detect and quantify any desired radioisotope eluted from a radioisotope generator that releases a daughter radioisotope produced via radioactive decay of a corresponding parent radioisotope. For example, in different applications, a radioisotope generator can produce a positron emitter, a photon emitter, or a particle emitter for therapy. The parent radioisotope is typically bound to a generator column through which an eluant is flushed during operation. As the parent radioisotope decays, one or more daughter radioisotopes are produced that bind to the generator column less strongly than the parent radioisotope. As a result, the daughter radioisotope may be released into the eluant flowing through the generator, thereby producing an eluate containing the daughter radioisotope.

In accordance with some example systems and techniques described herein, the eluate produced by the radioisotope generator is monitored to track both the volume of eluate produced by the radioisotope generator and an activity of one or more radioisotopes of interest in the eluate. The one or more radioisotopes of interest may be a parent radioisotope of the type bound on the radioisotope generator. The tracked volume may be correlated to the tracked activity to develop a correlation between the volume and activity. The correlation may then be extrapolated from a current cumulative volume of eluate and a current activity of the tracked radioisotope to a predicted cumulative volume of eluate at which the activity of the tracked radioisotope will reach a threshold. In some application, the volume of eluate may continue to be tracked and, upon reaching the predicted cumulative volume of eluate at which the activity of the tracked radioisotope will reach the threshold, shutdown or otherwise taken out of service and prevented from being used for further patient infusion procedures (e.g., until the radioisotope generator in the system is replaced).

Figure 1:
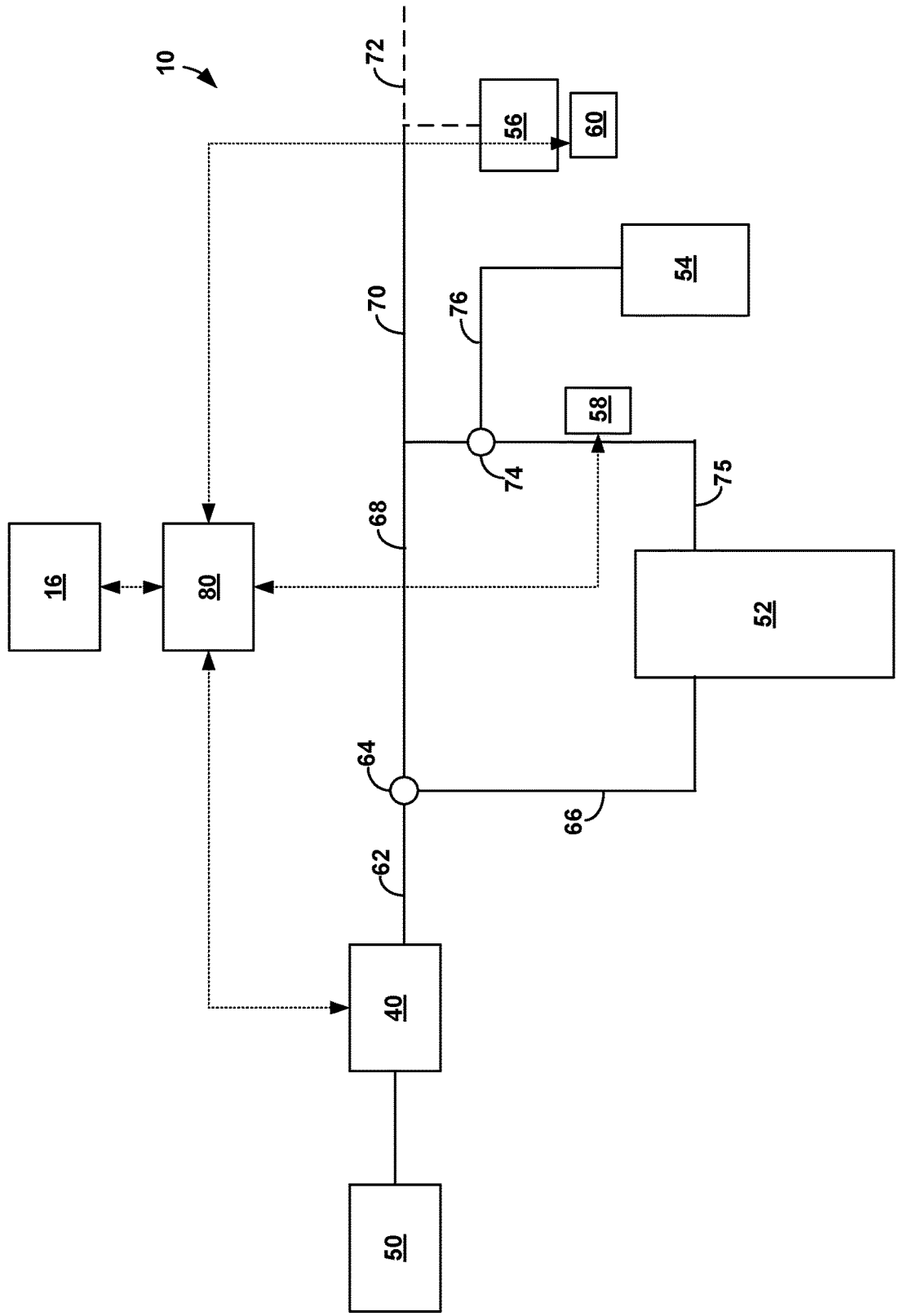
FIG. 1 is a block diagram illustrating an example radioisotope generator system in which the activity of a radioactive radioisotope and volume of eluate may be tracked to predict a replacement time for a radioisotope generator.

FIG. 1 is a block diagram illustrating an example radioisotope generator system 10 in which the activity of one or more radioisotopes of interest may be tracked along with a cumulative volume of eluate produced by the system and a predicted eluate volume determined at which the radioisotopes may reach a threshold. In the example, system 10 includes an eluant reservoir 50, an eluant pump 40, a radioisotope generator 52, a waste container 54, an eluate-receiving reservoir 56, a controller 80, and a user interface 82. System 10 also includes at least one activity detector, which is illustrated as being implemented using two activity detectors: a beta detector 58 and a gamma detector 60. One or more fluid tubing lines can connect the various components of system 10 together.

For example, in the configuration of FIG. 1, pump 40 receives eluant from eluant reservoir 50, pressurizes the eluant, and discharges pressurized eluant into an eluant line 62. A first diverter valve 64 controls the flow of eluant to one of a radioisotope generator inlet line 66 and a radioisotope generator bypass line 68. Eluant flowing through radioisotope generator bypass line 68 bypasses radioisotope generator 52 and can flow directly into an infusion tubing line 70. Infusion tubing line 70 can be in fluid communication with either eluate-receiving container 56 (e.g., during a quality control procedure) or a patient catheter 72 (e.g., during a patient infusion procedure). A second multi-way valve 74 controls a flow of eluate generated by elution within radioisotope generator 52 and received from a radioisotope generator discharge line 75 to either the infusion tubing line 70 or a waste line 76. Waste line 76 can be connected to waste container 54.

During operation, radioisotope generator 52 can generate radioisotopes via elution. For example, radioisotope generator 52 may be a strontium-rubidium generator containing strontium-82 bound on a support material, such as stannic oxide or tin oxide. Rubidium-82 is a daughter decay product of strontium-82 and binds less strongly to the support material than the strontium. As pressurized eluant from eluant reservoir 50 is passed through the radioisotope generator, the eluant may release rubidium-82 so as to generate an eluate. For example, when the eluant is a saline (NaCl) solution, sodium ions in the saline can displace rubidium in the generator so as to elute a rubidium-82 chloride solution.

In other examples, radioisotope generator 52 can generate different types of decay products besides rubidium-82. The type of daughter decay product produced by radioisotope generator 52 can be controlled by selecting the type of radioisotope loaded onto the generator support material. Example types of radioisotope generators that can be used as radioisotope generator 52 include, but are not limited to, $^{99}$Mo/$^{99m}$Tc (parent molybdenum-99 bound on a support material to produce daughter decay product technetium-99m); $^{90}$Sr/$^{90}$Y (parent strontium-90 bound on a support material to produce daughter decay product yttrium-90); $^{188}$W/$^{188}$Re (parent tungsten-188 bound on a support material to produce daughter decay product rhenium-188); and $^{68}$Ge/$^{68}$Ga (parent germanium-68 bound on a support material to produce daughter decay product gallium-68). Yet other types of radioisotope generators that can be used as radioisotope generator 52 include: $^{42}$Ar/$^{42}$K; $^{44}$Ti/$^{44}$Sc; $^{52}$Fe/$^{52m}$Mn; $^{72}$Se/$^{72}$As; $^{83}$Rb/$^{83m}$Kr; $^{103}$Pd/$^{103m}$Rh; $^{109}$Cd/$^{109m}$Ag; $^{113}$Sn/$^{113m}$In; $^{118}$Te/$^{118}$Sb; $^{132}$Te/$^{132}$I; $^{137}$Cs/$^{137m}$Ba; $^{140}$Ba/$^{140}$La; $^{134}$Ce/$^{134}$La; $^{144}$Ce/$^{144}$Pr; $^{140}$Nd/$^{140}$Pr; $^{166}$Dy/$^{166}$Ho; $^{167}$Tm/$^{167m}$Er; $^{172}$Hf/$^{172}$Lu; $^{178}$W/$^{178}$Ta; $^{191}$Os/$^{191m}$Ir; $^{194}$Os/$^{194}$Ir; $^{226}$Ra/$^{222}$Rn; and $^{225}$Ac/$^{213}$Bi.

To measure the radioactivity of one or more radioisotopes in the radioactive eluate generated via elution in system 10, the system may include one or more activity detectors configured to receive and measure different radioactive emissions produced by the radioactive eluate. For example, as shown in the example of FIG. 1, system 10 may include a beta detector 58 and a gamma detector 60. Beta detector 58 can be positioned downstream of radioisotope generator 52 to measure beta emissions emitted by radioactive eluate produced by the generator. Gamma detector 60 can also be positioned downstream of radioisotope generator 52 to measure gamma emissions emitted by the radioactive eluate produced by the generator.

The specific locations of beta detector 58 and gamma detector 60 can vary. However, in the example of FIG. 1, beta detector 58 is positioned between an outlet of radioisotope generator 52 and second multi-way valve 74, which is upstream of waste container 54 and infusion tubing 70 along the fluid pathway from the radioisotope generator. By contrast, gamma detector 60 is positioned downstream of the outlet of the radioisotope generator 52 and beta detector 58. For example, gamma detector 60 may be positioned downstream of the second multi-way valve 74 along the fluid pathway of infusion tubing 70.

In operation, beta detector 58 can measure beta emissions emitted by radioactive eluate generated by and discharged from radioisotope generator 52. In some examples, beta detector 58 is positioned in close proximity to radioisotope generator discharge line 75 such that the beta detector can detect beta emissions emitted from radioactive eluate present in the discharge line. The radioactive eluate may be flowing through the radioisotope generator discharge line 75 toward infusion tubing 70 and/or waste line 76. Alternatively, the radioactive eluate may be supplied to the radioisotope generator discharge line 75 and held static (non-flowing) while the beta detector 58 measures beta emissions emitted from the radioactive eluate. In yet other configurations, an eluate-receiving reservoir may be provided in fluid communication with radioisotope generator discharge line 75, for example via an additional multi-way valve, and beta detector 58 positioned to measure beta emissions from the radioactive eluate supplied to the eluate-receiving reservoir. In any configuration, beta detector 58 may measure beta emissions from radioactive eluate generated by the generator in order to detect and/or quantify one or more radioisotopes present in the radioactive eluate.

System 10 also includes a gamma detector 60. In operation, gamma detector 60 can measure gamma emissions emitted by radioactive eluate generated by and discharged from radioisotope generator 52. For example, radioactive eluate generated by radioisotope generator 52 may be discharged through radioisotope generator discharge line 75, diverter valve 74, infusion tubing 70, and supplied to eluate-receiving container 56. Gamma detector 60 may be positioned in close proximity to eluate-receiving container 56 in order to detect gamma emissions emitted by the portion of radioactive eluate delivered to the receiving container. For example, a clinician may attach an outlet of infusion tubing 70 to an inlet of eluate-receiving container 56 in order to supply radioactive eluate to the receiving container. Upon subsequently controlling pump 40 to generate radioactive eluate that is supplied to the eluate-receiving container 56, gamma detector 60 may measure gamma emissions emitted by the radioactive eluate.

While FIG. 1 illustrates one example location for gamma detector 60, other locations may be used. For example, gamma detector 60 may be positioned in close proximity to a tubing line downstream of radioisotope generator 52, such as radioisotope generator discharge line 75 and/or infusion tubing 70. In these examples, gamma detector may measure gamma emissions emitted by radioactive eluate flowing through the tubing line or a static (non-flowing) portion of radioactive eluate held within the tubing line. Independent of the specific location of the gamma detector within system 10, gamma detector 60 may measure gamma emissions from radioactive eluate generated by the radioisotope generator 52 in order to detect and/or quantify one or more radioisotopes present in the radioactive eluate.

For example, gamma emissions measured by gamma detector 60 may be used to detect and/or quantify one or more contaminating radioisotopes in radioactive eluate generated by radioisotope generator 52, while beta emissions measured by beta detector 58 may be used to detect and/or quantify one or more radioisotopes in the radioactive eluate targeted for patient infusion. In some examples, beta detector 58 measures beta emissions from radioactive eluate flowing through radioisotope generator discharge line 75 toward eluate-receiving container 56. Once the radioactive eluate has passed beta detector 58 and filled eluate-receiving container 56, either partially or fully, gamma detector 60 may measure gamma omissions from that portion of radioactive eluate supplied to the receiving container. In these applications, gamma detector 60 may measure gamma emissions from a portion of radioactive eluate also emitting beta emissions which were detected by beta detector 58 as the radioactive eluate flowed towards the eluate-receiving container 56. In other operational configurations, beta detector 58 and gamma detector 60 may not measure radioactive emissions from the same portion or volume of radioactive eluate but may measure radioactive emissions from different portions of radioactive eluate.

Radioisotope generator system 10 in the example of FIG. 1 also includes a controller 80. Controller 80 may be communicatively coupled (e.g., via a wired or wireless connection) to the various pump(s), valves, and other components of system 10, including beta detector 58 and gamma detector 60, so as to send and receive electronic control signals and information between controller 80 and the communicatively coupled components. For example, controller 80 may receive data generated by beta detector 58 indicative of the magnitude of beta emissions detected by the detector. Controller 80 may further receive data generated by gamma detector 60 indicative of the amount and type (e.g., spectral distribution) of gamma emissions detected by the detector. Controller 80 may further process the data to determine an activity of different radioisotopes in the eluate from which beta detector 58 and gamma detector 60 detected beta emissions and gamma emissions, respectively. Controller 80 may also manage the overall operation of radioisotope generator system 10, including initiating and controlling patient dosing procedures, controlling the various valves and pump(s) in the system, receiving and processing signals from beta detector 58 and gamma detector 60, and the like.

In operation, beta detector 58 can detect beta emissions emanating from radioactive eluate positioned in front of the detector. Beta detector 58 can include a variety of components to detect and process beta emission signals. In some configurations, beta detector 58 is implemented using a solid-state detector element such as a PIN photodiode. In these configurations, the solid-state detector element can directly convert impinging radioactive energy into electrons in the semiconductor material of the detector. The electrons can then be amplified into an usable signal (e.g., received by controller 80). In some examples, beta detector 58 includes a scintillator, which converts impinging radioactive energy into light pulses, which is then captured by an attached photon-to-electron converter such as a photomultiplier tube or avalanche photodiode. The choice of the scintillator can determine the sensitivity and the countrate performance. For example, beta detector 58 may be implemented using a plastic scintillator when high sensitivity and high countrate performance are desired.

During operation, gamma detector 60 can detect gamma ray emissions emanating from a portion of eluate positioned in close proximity to the detector, e.g., statically positioned in eluate-receiving container 56. Gamma detector 60 may include a variety of different components to detect and process gamma ray radiation signals, such as a pulse sorter (e.g., multichannel analyzer), amplifiers, rate meters, peak position stabilizers, and the like. In one example, gamma detector comprises a scintillation detector. In another example, gamma detector comprises a solid-state semiconductor detector.

The specific type of gamma detector selected for detector 60 can vary based on a variety of factors such as, e.g., the required resolution of the detector, the physical requirements for practically implementing the detector in a system (e.g., cooling requirements), the expected sophistication of the personnel operating the detector, and the like. In some applications, gamma detector 60 is a non-ion-chamber type gamma detector (e.g., a detector that measures gamma emissions and does not include an ion chamber). In some applications, gamma detector 60 is a scintillator-type detector, such as a comparatively low-resolution alkali halide (e.g., NaI, CsI) or bismuth germanate (e.g., Bi4Ge3O12, or BGO). In other applications, gamma detector 60 incorporates a higher-Z metallic species. An example is lutetium oxyorthosilicate, Lu2(SiO4)O(Ce) or LSO, which, though slightly better in resolution than BGO, may have limited applicability because of its relatively high intrinsic radiation. As another example, gamma detector 60 may be a cerium-doped lanthanum, such as LaCl3(Ce) or LaBr3(Ce).

In other applications, gamma detector 60 is a solid-state semiconductor-type detector, such as a planar germanium detector. For instance, as another example, gamma detector 60 may be a solid-state semiconductor-type telluride detector, such as cadmium-telluride or cadmium-zinc-telluride semiconductor detector. Gamma detector 60 may be operated at room (ambient) temperature or may be cooled below room temperature (e.g., by a cooling device incorporated into radioisotope generator system 10) to increase the resolution of the detector.

Gamma detector 60 can generate gamma ray spectroscopy data. For example, the detector may include a passive material that waits for a gamma interaction to occur in the detector volume. Example interactions may be photoelectric effects, Compton effects, and pair production. When a gamma ray undergoes a Compton interaction or pair production, for instance, a portion of the energy may escape from the detector volume without being absorbed so that the background rate in the spectrum is increased by one count. This count may appear in a channel below the channel that corresponds to the full energy of the gamma ray.

A voltage pulse produced by gamma detector 60 can be shaped by a multichannel analyzer associated with the detector. The multichannel analyzer may take a small voltage signal produced by the detector, reshape it into a Gaussian or trapezoidal shape, and convert the signal into a digital signal. The number of channels provided by the multichannel analyzer can vary but, in some examples, is selected from one of 512, 1024, 2048, 4096, 8192, or 16384 channels. The choice of the number of channels may depend on the resolution of the system, the energy range being studied, and the processing capabilities of the system.

Data generated by gamma detector 60 in response to detecting gamma ray emissions may be in the form of a gamma ray spectrum that includes peaks. The peaks may correspond to different energy levels emitted by different radioisotopes within an eluate sample under analysis. These peaks can also be called lines by analogy to optical spectroscopy. The width of the peaks may be determined by the resolution of the detector, with the horizontal position of a peak being the energy of a gamma ray and the area of the peak being determined by the intensity of the gamma ray and/or the efficiency of the detector.

During operation, controller 80 may receive data generated by beta detector 58 and/or gamma detector 60 indicative of beta emissions and gamma emissions detected by the respective detectors. Controller 80 may process the data to determine an activity of one or more radioisotopes in the radioactive eluate from which beta detector 58 and/or gamma detector 60 detected beta emissions and/or gamma emissions, respectively. Controller 80 may manage operation of system 10 based on the determined activity of the one or more radioisotopes.

System 10 can operate in a number of different modes, including a patient infusion mode and a quality control mode. During a patient infusion procedure, an infusion tubing circuit (e.g., infusion tubing 70) can connect an outlet of the radioisotope generator to a patient catheter. The infusion tubing circuit can be positioned adjacent the beta detector such that, as eluate flows through the infusion tubing circuit, the eluate passes over the beta detector. Beta emissions emitted by the eluate can be detected by the beta detector and the activity of a radioisotope associated with those beta emissions determined.

During a quality control procedure, by contrast, an infusion tubing line (e.g., infusion tubing 70) in fluid communication with the outlet of the radioisotope generator may be attached to the eluate-receiving container instead of a patient catheter. During this quality control procedure, the radioisotope generator may produce radioactive eluate that flows through the tubing line, past the beta detector, and into the eluate-receiving container. The beta detector may measure beta emissions from the radioactive eluate as it flows through the infusion tubing, e.g., to determine an activity level of rubidium-82 in the eluate. The gamma detector may receive gamma emissions from eluate in the eluate-receiving container, e.g., to determine an activity level of a radioisotope of interest (e.g., parent radioisotope) such as strontium-82, strontium-85, and/or other contaminants in the eluate.

For example, when radioisotope generator 52 is implemented using a strontium-rubidium radioisotope generator, controller 80 may receive data from beta detector 58 indicative of beta emissions measured from radioactive eluate flowing through radioisotope generator discharge line 75. Controller 80 may not be able to resolve different radioisotopes from the beta emissions measured by beta detector 58 but may instead be programmed to assume that all such beta emissions are attributable to radioactive rubidium-82 present in the radioactive eluate, since rubidium may be expected to be the predominant radioactive species present. Accordingly, with reference to data stored in memory, controller 80 may determine an activity of rubidium present in the radioactive eluate supplied from radioisotope generator 52 based on a cumulative magnitude of beta emissions measured by beta detector 58.

Controller 80 may further receive in such examples data from gamma detector 60 indicative of gamma emissions measured from a portion of radioactive eluate supplied to eluate-receiving container 56. Controller 80 may determine which species of one or more other radioisotopes are present in the radioactive eluate and/or an activity level of those species based on the received data from the gamma detector. For example, controller 80 may determine which species of radioisotopes and/or an activity of those radioisotopes are present in the radioactive eluate based on the amount and type (e.g., spectral distribution) of gamma emissions detected by gamma detector 60. For instance, controller 80 may determine an activity of strontium-82 and/or strontium-85 present in the radioactive eluate, if any, which can be contaminants to the rubidium-82 radioisotope intended for patient infusion procedure.

A quality control procedure using system 10 may be executed on a periodic basis to determine an activity of one or more radioisotopes of interest in the eluate produced by radioisotope generator 52. For example, a quality control test may be performed at a frequency ranging from multiple times per day (e.g., two, three, or four times per day) to once every 30 days, such as once every day to once every 15 days, or from once per day to once every 10 days, such as approximately daily, at least every 3 days, at least every 5 days, or at least every 7 days.

Independent of the frequency with which activity measurements are made to quantify the activity of one or more radioisotopes of interest in the eluate generated by radioisotope generator 52, controller 80 may track the activity of the one or more radioisotopes of interest as measured during the quality control procedure. For example, controller 80 may track the activity of the radioisotope by storing a value indicative of the activity in a non-transitory computer readable memory associated with the controller. The activity may be stored in the form of one or more values, and may be stored in a table or other data structure usable by controller 80. Controller 80 may track the activity of the one or more radioisotopes of interest by storing a value indicative of the activity determined during each quality control procedure performed since the beginning of the service life of the generator (e.g., the generator is newly filled or refilled and installed in system 10). Alternatively, controller 80 may track the activity of the one or more radioisotopes of interest by storing a value indicative of the activity determined during each quality control procedure after a threshold amount of eluate has been generated by the system, such as at least 100 ml, at least 500 ml, at least 1 liter, or at least 2 liters.

Controller 80 can also track a cumulative volume of radioactive eluate generated by radioisotope generator 52. In general, the volume of eluant introduced into radioisotope generator 52 is the same as the volume of eluate produced by the generator. Accordingly, controller 80 may track the cumulative volume of radioactive eluate generated by radioisotope generator 52 by tracking the eluate itself and/or by tracking the volume of eluant supplied to the radioisotope generator, thereby deriving the volume of radioactive eluate generated by radioisotope generator 52.

In some examples, system 10 includes one or more volume sensors (e.g., flow rate sensors) that measure the volume of eluant introduced into generator 52 and/or eluate discharging from the generator. Controller 80 can receive a signal from the one or more volume sensors indicative of the volume of eluate produced by radioisotope generator 52. Additionally or alternatively, controller 80 may receive information indicative of a volume of eluant pumped by pump 40 which, in turn, provides data concerning the volume of eluate produced by generator 52. Pump 40 may be implemented as a syringe pump, peristaltic pump, piston pump, or yet other fluid conveyance device, e.g., with a motor driving the pump. Controller 80 may receive a signal from a displacement sensor monitoring a position of pump 40 (and hence the corresponding volume expected to be delivered by the pump based on position), a sensor monitoring an amount of electrical power (e.g., current) drawn by the motor of pump 40 during operation (and hence the corresponding volume expected to be delivered by the pump based on the power), and/or other information concerning the volume of fluid moved by pump 40 into and through radioisotope generator 52.

Controller 80 may track the cumulative volume of eluate produced by radioisotope generator 52 by storing one or more values indicative of the volume of eluate produced by the generator in a non-transitory computer readable memory associated with the controller. Controller 80 may track the cumulative volume by generating a sum or total volume of eluate generated by radioisotope generator 52 from a plurality of individual volumes generated by the radioisotope generator and measured. Since individual volumes generated by radioisotope generator 52 and measured (e.g., tracked) may include all eluant delivered to the generator (and, correspondingly all eluate discharging from the generator), including when the eluate is delivered to a patient, waste reservoir 54, and to eluate-receiving container 56 through multiple runs following installation in system 10, the cumulative volume can be tracked by the system. The cumulative volume may be stored in the form of one or more values, and may be stored in a table or other data structure usable by controller 80. Controller 80 may track the cumulative volume eluate produced by radioisotope generator 52 by storing one or more values indicative of the volume of eluate produced by the generator each time eluate is produced by the generator.

Controller 80 may track the volume of eluate produced by radioisotope generator 52 from a time when the radioisotope generator is initially installed in system 10 and communicatively coupled with controller 80 (e.g., the generator is newly filled or refilled and installed in system 10). This may be designated as the beginning of the service life of the radioisotope generator and may or may not exclude any eluate produced by the generator prior to installation in system 10, such as a limited amount of eluate that may be produced during testing and qualification prior to installation of the generator in system 10. Alternatively, controller 80 may start tracking the volume of eluate produced by radioisotope generator 52 a given period of time after the radioisotope generator is initially installed in system 10 and communicatively coupled with controller 80. This given period of time can be at least one day, at least 2 days, at least 5 days, at least 7 days, at least 14 days, at least 21 days, at least 28 days, at least 35 days, or any given time during the life of the generator.

Additionally or alternatively, controller 80 may track the cumulative volume a period of time after a threshold amount of eluate has been generated by the system, such as at least 100 ml, at least 500 ml, at least 1 liter, at least 2 liters, at least 5 liters, at least 10 liters, or any given volume during the life of the generator.

As briefly discussed above, radioisotope generator 52 may release one or more radioisotope into the eluate that is undesired (e.g., is not targeted for injection into a patient for clinical use). The activity of these one or more undesired radioisotopes released into the eluate may increase over the operational life of radioisotope generator 52. Initially, the activity of the undesired radioisotope in the eluate produced by radioisotope generator 52 may be sufficiently low that the eluate produced by the generator is suitable for introduction into a human patient. Over continued service as the cumulative volume of eluate produced by radioisotope generator 52 increases, the activity of the undesired radioisotope in the eluate produced by radioisotope generator 52 may increase to a level where it is unsuitable to be introduced into a patient.

The specific threshold(s) at which the activity level of the undesired radioisotope(s) in the eluate produced by radioisotope generator 52 may reach (e.g., equal and/or exceed) before being designated as unsuitable for injection into a patient may vary, e.g., depending on the type of generator used. In the case of a Sr-82/Rb-82 radioisotope generator that produces radioactive rubidium-82 from a radioisotope generator containing strontium-82, the threshold may be a Sr-82 level of less than 0.05 μCi per millicurie of Rb-82, such as less than 0.02 μCi per millicurie of Rb-82, about 0.02 μCi per millicurie of Rb-82, less than 0.01 μCi per millicurie of Rb-82, or about 0.01 μCi per millicurie of Rb-82. For example, the threshold may be a strontium-82 activity less than 0.02 μCi, such as a strontium-82 activity between 0.002 μCi and 0.02 μCi, or a strontium-82 activity of 0.01. Additionally or alternatively, the threshold may be a Sr-85 level of 0.5 μCi per millicurie of Rb-82, such as less than 0.2 μCi per millicurie of Rb-82, about 0.2 μCi per millicurie of Rb-82, less than 0.1 μCi per millicurie of Rb-82, or about 0.1 μCi per millicurie of Rb-82. Any threshold may be stored in a memory associated with controller 80.

Controller 80 can determine a predicted volume of the radioactive eluate generated by the radioisotope generator at which the activity of an undesired radioisotope in the radioactive eluate will reach a threshold (e.g., stored in a memory associated with the controller). Rather than waiting for the cumulative volume of eluate produced by radioisotope generator 52 to reach a point where the activity of the undesired radioisotope in the eluate is at a level unsuitable to be introduced into a patient, controller 80 may predictively determine what this cumulative volume will be prior to reaching the activity level. Controller 80 can determine the predicted volume at which the activity of the undesired radioisotope in the radioactive eluate will reach a threshold based on the tracked cumulative volume of the radioactive eluate produced by radioisotope generator 52 and the tracked activity of the undesired radioisotope.

For example, controller 80 can analyze the tracked cumulative volume of the radioactive eluate produced by radioisotope generator 52 and the tracked activity of the undesired radioisotope and determine a relationship between the tracked volume and tracked activity. For example, controller 80 may perform a curve fitting process such as a regression analysis to determine a relationship between the tracked volume and the tracked activity. The determined relationship (or coefficients associated therewith) can then be stored.

For example, controller 80 may fit a curve representing tracked activity plotted on a y-axis of a graph with corresponding cumulative volume data plotted on the x-axis of the graph. Controller 80 may fit a first order curve having a slope and an intercept or a higher order curve (e.g., second order, third order, or higher), with additional coefficients corresponding to the higher order curve. The curve and/or coefficients thereof may be stored in memory. Controller 80 may employ any suitable statistical software package such as, e.g., Minitab, Excel, or the like, to generate the relationship.

In addition, controller 80 may extrapolate the determined relationship from a current cumulative volume of eluate produced by radioisotope generator 52 to a volume at which the corresponding activity of the undesired radioisotope will be at a threshold. The volume at this extrapolation can be deemed the predicted volume at which the activity of the undesired radioisotope in the radioactive eluate will reach the threshold.

In some examples, controller 80 is configured to determine the predicted volume a plurality of times, each time (or at a lesser frequency) in response to receiving new data concerning the cumulative volume of radioactive eluate generated by radioisotope generator 52 and/or the activity of an undesired radioisotope in the radioactive eluate generated by the radioisotope generator. As new tracked volume and activity data are received by controller 80 longer in the service life of radioisotope generator 52, controller 80 may be able to refine and determine the predicted volume with increasing accuracy.

It should be appreciated that while the foregoing tracking and determination of the predicted volume are described as being performed by controller 80 (which also controls system 10), the computing functionality attributed to controller 80 in system 10 may be performed on any one or more controllers associated with the system, be it physically on system 10 or remotely located, and the functionalities described herein are not limited to being performed on any specific hardware device. For example, system 10 and controller 80 may communicate with an external device, such as a remote server, cloud-computing environment, or other physically remote computing device performing some or all of the computing functionality described herein. That being said, in other configurations, one or more controllers located on system 10 (e.g., on a mobile cart or platform associated with components of the system) may perform some or all of the controller functions described herein.

Controller 80 may take a variety of actions in response to determining the predicted volume. As one example, controller 80 may initiate a user alert (e.g., a visual, textual, audible user alert), e.g., by controlling user interface 16 to deliver the alert concerning the predicted volume and/or remaining volume that can be eluted by the generator before reaching the predicted volume. As another example, controller 80 may continue tracking the cumulative volume of eluate produced by radioisotope generator 52 and compare the tracked cumulative volume against the predicted volume. Controller 80 may terminate elution using radioisotope generator or otherwise prevent a patient infusion procedure (e.g., by controlling pump 40 to cease generating eluate and/or controlling second multi-way valve 74 to divert elute from infusion tubing 70 to waste line 76) when the tracked cumulative volume equals the predicted volume or is within a threshold of the predicted volume (e.g., within 10% of the predicted volume, such as within 5% of the predicted volume, within 2% of the predicted volume, or within 1% of the predicted volume). In some examples, an operator or party responsible with maintaining system 10 may replace radioisotope generator 10 with a fresh generator when the cumulative volume reaches or is within the threshold of the predicted volume.

As noted, system 10 may include a user interface 16. User interface 16 may include a display screen as illustrated or other output media, and user input media. For example, user interface may include a keyboard, mouse, depressible buttons, switches, and/or touch screen interface. In some examples, user interface 16 may be configured to provide visual, audible, and/or tactile feedback to a user. User interface 16 may be communicatively coupled to a controller that controls the operation of system 10. A clinician or other user may interact with system 10 through user interface 16, e.g., to change or establish the parameters of a patient infusion procedure, change or establish the parameters of a quality control procedure, view historical or maintenance information, or otherwise interact with system 10. In one example, user interface 16 is implemented as a touchscreen having a screen that a user can physically touch to communicate with system 10.

As further noted above, system 10 may include a waste container 54 and in eluate-receiving container 56. Waste container 54 and eluate-receiving container 56 may each be structures configured to receive and hold liquid received from upstream tubing. In different examples, waste container 54 and/or eluate-receiving container 56 may be reservoirs permanently formed in a shielding assembly containing radioisotope generator 52 or maybe removable from the shielding assembly. For example, waste container 54 and/or eluate-receiving container 56 may be a vessel (e.g., bottle, vial, canister, or other receptacle) configured to receive radioactive eluate, each of which is removable from a shielding assembly containing radioisotope generator 52.

In general, waste container 54 is intended to receive radioactive eluate produced upon activation of system 10, as pump 40 pumps eluant through radioisotope generator 52 toward waste container 54. For example, in operation, pump 40 may pump eluant through radioisotope generator 52 while controller 80 controls second multi-way valve 74 to direct radioactive eluate toward waste container 54. Upon determining that the radioactive eluate produced by radioisotope generator 52 has a threshold level of activity, controller 80 may control second multi-way valve 74 to direct the radioactive eluate to infusion tubing 70 (and to patient catheter 72 or eluate-receiving container 56 coupled thereto) instead of toward waste container 54. Controller 80 may determine that the radioactive eluate produced by radioisotope generator 52 has a threshold level of activity based on the beta emissions measured by beta detector 58, e.g., and threshold information stored in memory associated with the controller. In different examples, waste container 54 may be sized to hold a volume of liquid received from radioisotope generator 52 of at least 100 mL, such as at least 250 mL, or greater than or equal to 500 mL. As one example, waste container 54 may be sized to hold from 250 mL to 1 L.

In contrast to waste container 54 which is intended to receive radioactive eluate produced by radioisotope generator 52 that is designated as waste, eluate-receiving container 56 can receive patient-infusible radioactive eluate produced by the radioisotope generator. Eluate-receiving container 56 may receive and hold a portion of the radioactive eluate produced by the radioisotope generator (e.g., after controller 80 has actuated multi-way valve 74 to redirect the radioactive eluate being produced from waste line 76 to infusion tubing 70). While eluate-receiving container 56 is being filled with radioactive eluate and/or after the eluate-receiving container has filled, gamma detector 60 may measure gamma emissions emanating from the radioactive eluate. In some examples, beta detector 58 measures beta emissions from radioactive eluate flowing through radioisotope generator discharge line 75 as the eluate flows to eluate-receiving container 56, whereupon gamma detector 60 measures gamma omissions from that same portion of eluate whose beta emissions were previously measured by the beta detector.

Controller 80 may determine an activity of one or more radioisotopes present in the radioactive eluate received by an eluate-receiving container 56 based on the gamma emissions measured by gamma detector 60. This activity may be tracked by controller 80 as discussed above to determine a predicted volume of the radioactive eluate generated by the radioisotope generator at which the activity of an undesired radioisotope in the radioactive eluate will reach a threshold.

Although eluate-receiving container 56 can have a number of different configurations, in some examples, the eluate-receiving container is sized smaller than waste container 54. For example, eluate-receiving container 56 may be sized to receive and hold a volume of liquid less than 500 mL, such as less than 250 mL or less than 100 mL. In one example, eluate-receiving container is sized to hold from 10 mL to 100 mL. Further, while eluate-receiving container 54 can be implemented using a variety of different types of containers, in some examples, the eluate-receiving container is fabricated of glass or plastic, such as a glass vial or bottle, or a plastic syringe or container. Such a structure may be useful in that the glass vial may limit the extent to which gamma emissions are blocked or attenuated by the eluate-receiving container, allowing gamma detector 60 to adequately detect gamma emissions emitted by the radioactive eluate delivered to the container.

In practice, eluate-receiving container 56 may be reused for multiple quality control procedures or may be disposable after each quality control procedure. For instance, in some applications, an operator may select a new, previously unused, eluate-receiving container and insert the container into an appropriate compartment of a shielding assembly containing radioisotope generator 52. After performing the quality control procedure, the operator can remove the eluate-receiving container, discard the contents of the container appropriately, and then discard the container itself. Typically, waste container 54 is a reusable structure, for example fabricated from metal, glass, or other compatible material, that may be removed and emptied from a shielding assembly containing radioisotope generator 52 periodically but is not discarded after each use.

Some or all of the components of system 10 may be contained within a shielding assembly. The shielding assembly can house various components of system 10 exposed to and/or in contact with radioactive eluate. In general, the shielding assembly may be formed of one or more materials that provide a barrier to radioactive radiation. The type of material or materials used to fabricate the shielding assembly and the thicknesses of those materials may vary, for example, depending on the type and size of radioisotope generator 52 used in the system and, correspondingly, the amount of radiation shielding needed. In general, the thickness and/or configuration of the radiation shielding material used to form the shielding assembly may be effective to attenuate radiation emanating from inside of the shielding assembly to a level which is safe for operating personnel to work around system 10. For example, when a new strontium-rubidium generator is installed in the shielding assembly, it may contain 200 millicuries of radioactivity. The shielding assembly may block the emitted radiation so the radiation level outside of the shielding assembly does not exceed that which is allowable for operating personnel surrounding the shielding assembly. In some examples, the shielding assembly is fabricated from lead or lead alloys or other high density materials, e.g., and may have a wall thickness greater than 25 millimeters.

Additionally, in some examples, system 10 (including any shielding assembly) may be installed on a frame that defines a mobile cart frame. For example, the components of system 10 may be physically and/or mechanically connected (directly or indirectly) to a frame that carries the components. The frame may be mounted on wheels so as to be movable. Additional details on radioisotope generator systems that may be used in accordance with the disclosure are described in PCT/US17/52537, filed Sep. 20, 2017, the entire contents of which are incorporated herein by reference.

Figure 2:
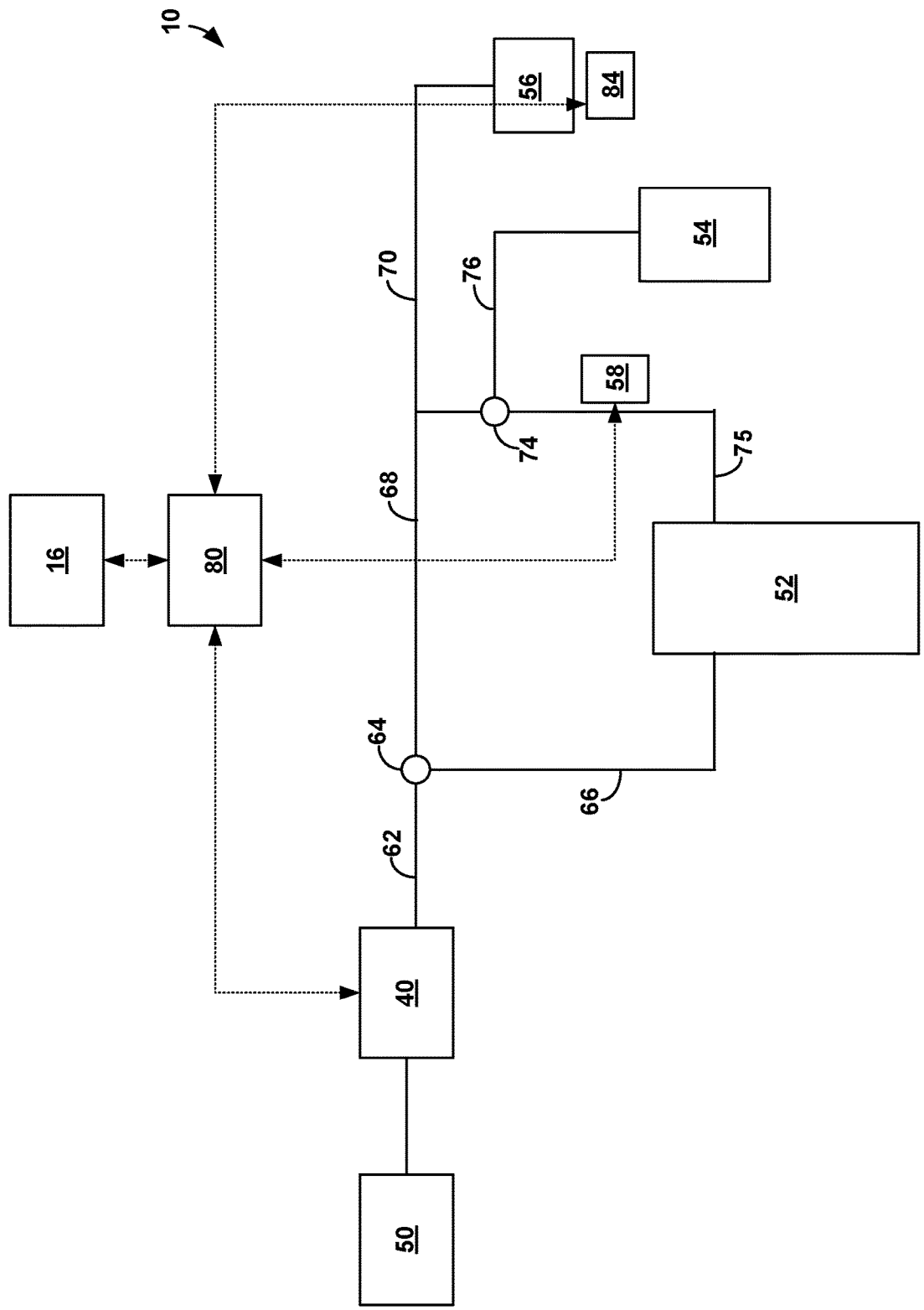
FIG. 2 is a block diagram illustrating another example configuration of an example radioisotope generator system in which the activity of a radioactive radioisotope and volume of eluate may be tracked to predict a replacement time for a radioisotope generator.

FIG. 2 is a block diagram illustrating another example configuration of radioisotope generator system 10 where like reference numerals refer to like elements discussed above with respect to FIG. 1. The example configuration of system 10 in FIG. 2 is different than the configuration in FIG. 1 in that system 10 in FIG. 2 includes a dose calibrator 84 to measure an activity of radioactive eluate produced by radioisotope generator 52 (in addition to or in lieu of beta detector 58) rather than gamma detector 60.

Dose calibrator 84 may be an instrument used to assay the activity of a radioactive material prior to clinical use. The objective of the assay can be to assure that the patient receives the prescribed dose for the diagnostic or therapeutic purpose. A dose calibrator typically includes an electrometer designed to measure a wide range of ionization current, spanning from femtoamperes (fA) for beta emitters up to tens of picoamperes (pA) for high-energy, high-yield photon emitters. Some high-activity assays can even involve microamperes (pA) currents. The accuracy of the electrometer depends upon the type and quality of the electrometer and the accuracy of the standard reference sources used to calibrate the electrometer. Dose calibrators generally have no intrinsic photon energy discrimination capability. Accordingly, a dose calibrator may not include a spectrometer and may not restrict the measurement to specific photon energies to the exclusion of others, which gamma detector 60 is capable of performing. For example, dose calibrator 84 may include an ion chamber whereas gamma detector 60 may lack an ion chamber (e.g., be a non-ion-chamber type gamma detector).

Activity measurements made by beta detector 58 may be distinguishable from those made by gamma detector 60 and/or dose calibrator 84. A beta detector can measure beta emissions caused by radioactive beta decay. During beta decay, a beta particle that is either an electron or a positron is emitted from an atomic nucleus. The beta detector can detect beta particles emitted from the radioactive eluate, allowing the activity level of a radioisotope assumed to be associated with those beta particles to be determined. By contrast, gamma detector 60 can measure gamma emissions or photons caused by radioactive gamma decay. During gamma decay, high-energy photons may be emitted from an atomic nucleus, providing detectable gamma rays. The energy level of the gamma rays may vary depending on the specific radioisotope from which the rays are emitted. Gamma detector 60 can detect the gamma emissions, for example by measuring a full or partial gamma spectrum, allowing the activity level of one or more radioisotopes to be determined. Further, gamma detector 60 may discriminate photons with different energy levels, unlike dose calibrator 84.

Dose calibrator 84 may be used to determine an activity of one or more undesired radioisotopes in eluate produced by radioisotope generator 52, e.g., for tracking and determination of the predicted volume. Dose calibrator 84 may be external to and separate from the other components of system 10 or may be integrated with the components of the system. For instance, in some examples, infusion tubing line 70 extends from system 10 to an eluate collection container positioned in a dose calibrator 84 located off board a mobile cart (e.g., on a counter or table adjacent to the cart) containing the other components of system. In other configurations, system 10 may include an onboard dose calibrator 84 that is contained on the mobile cart with the other components of the system and is movable therewith. In either case, controller 80 may receive data generated by the dose calibrator via wired or wireless communication with the dose calibrator and/or via user entry using user interface 16.

During quality control testing as discussed above with respect to FIG. 1, controller 80 can control system 10 to deliver radioactive eluate to the eluate collection container. To initiate the process, an operator may attach infusion tubing line 70 to eluate collection container 56 and interact with system 10 (e.g., via user interface 16) to elute a sample of eluate. The eluate collection container may or may not be inserted into a dose calibrator prior to initiating elution. The activity of the eluate received by the collection container 56 may be measured by dose calibrator 84 continuously from filling of the container through completion of the calibration measurement or at one or more discrete time periods during the quality control process. For example, the activity of the eluate in the container may be measured following the end of elution, when pump 40 ceases pumping eluant through radioisotope generator 52 to generate eluate or controller 80 controls multi-way valve 74 to direct the radioactive eluate to waste container 54 instead of the eluate collection container.

In some examples, dose calibrator 84 measures an activity of eluate supplied to the eluate-receiving container 56 after a period of time sufficient for substantially all the initial daughter radioisotope (e.g., Rb-82) in the radioactive eluate to decay. In some examples, the period of time sufficient for substantially all the initial daughter radioisotope to decay is at least 3 half-lives of the daughter radioisotope, such as at least 5 half-lives of the daughter radioisotope. In the case of Rb-82 which has a half-life of about 76 seconds, the period of time may be greater than 15 minutes, such as greater than 20 minutes, or greater than 30 minutes. For example, the period of time may range from 15 minutes to one hour, such as 25 minutes to 45 minutes. The resulting activity measurement made by dose calibrator 84 may be that of one or more undesired radioisotopes, such as Sr-82 and/or Sr-85 in the case of a Sr-82/Rb-82 radioisotope generator. Controller 80 (or other computing device) may determine the activity of the other strontium radioisotope with reference to a ratio stored in memory relating the activity of Sr-82 to the activity of Sr-85. The activity of Sr-82 may be related to the activity of strontinum-85 by a known radioisotope ratio, which may be stored in memory associated with controller 80. Controller 80 can determine the activity of one radioisotope by multiplying the determined activity of the other radioisotope by the stored ratio. In some examples, controller 80 sums the determined activity of Sr-82 and the determined activity of Sr-85 to identify the total strontium activity in the radioactive eluate. In either case, controller 80 can receive the activity information and track the activity information for determining a predicted volume at which the activity of the radioisotope in the radioactive eluate will reach a threshold, as discussed above with respect to FIG. 1.

Figure 3:
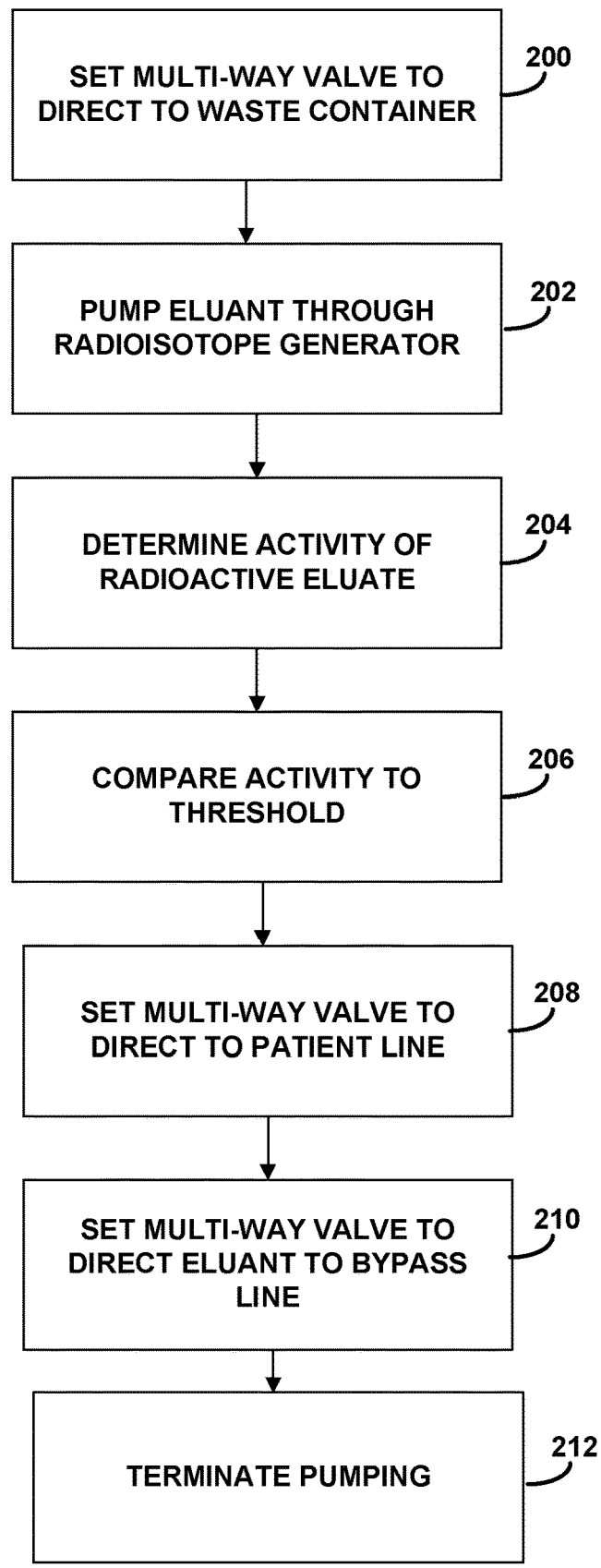
FIG. 3 is a flow diagram of an example technique that may be used to perform a patient infusion procedure to infuse radioactive liquid into a patient.

FIG. 3 is a flow diagram of an example technique that may be used to perform a patient infusion procedure to infuse radioactive liquid into a patient, e.g., during a diagnostic imaging procedure. For example, the technique of FIG. 3 may be used by system 10 to generate radioactive eluate and infuse the radioactive eluate into a patient. The technique of FIG. 3 will be described with respect to system 10, and more particularly the arrangement of exemplary components described with respect to FIG. 1 above, for purposes of illustration. However, it should be appreciated that the technique may be performed by systems having other arrangements of components and configurations (e.g., FIG. 2), as described herein.

To initiate a patient infusion procedure, an operator may interact with system 10 to set the parameters of the infusion and to initiate the infusion procedure. System 10 may receive parameters for the infusion via user interface 16, via a remote computing device communicatively coupled to system 10, or through yet other communication interfaces. Example parameters that may be set include, but are not limited to, the total activity to be dosed to a patient, the flow rate of radioactive eluate to be dosed to the patient, and/or the volume of radioactive eluate to be dosed to the patient. Once the appropriate parameters establishing the characteristics of the infusion procedure are programmed and stored, system 10 may begin generating radioactive eluate that is infused into the patient.

As shown in the example of FIG. 3, a patient infusion procedure may start by controlling second multi-way valve 74 to place radioisotope generator discharge line 75 in fluid communication with waste container 54 via waste line 76 (200). If second multi-way valve 74 is initially positioned so radioisotope generator discharge line 75 is in fluid communication with waste container 54, controller 80 may control system 10 to proceed with the infusion procedure without first actuating the valve. However, if second multi-way valve 74 is positioned so radioisotope generator discharge line 75 is in fluid communication with infusion tubing 70, controller 80 may control second multi-way valve 74 (e.g., by controlling an actuator associated with the valve) to place the radioisotope generator discharge line in fluid communication with the waste container. In some examples, controller 80 receives a signal from a sensor or switch associated with second multi-way valve 74 indicating the position of the valve and, correspondingly, which line radioisotope generator discharge line 75 is in fluid communication with through the valve.

In addition to or in lieu of controlling second multi-way valve 74, controller 80 may check the position of first multi-way valve 64 and/or control the valve to change the position of the valve before proceeding with the patient infusion procedure. For example, if first multi-way valve 64 is positioned to direct eluant through bypass line 68, controller 80 may control the valve (e.g., by controlling an actuator attached to the valve) to place eluant line 62 in fluid communication with the radioisotope generator inlet line 66. In some examples, controller receives a signal from a sensor or switch associated with first multi-way valve 64 indicating the position of the valve and, correspondingly, which line eluant line 62 is in fluid communication with the valve.

With first multi-way valve 64 positioned to direct eluant through radioisotope generator inlet line 66 and second multi-way valve 74 positioned to direct radioactive eluate from radioisotope generator discharge line 75 to waste container 54, controller 80 can control pump 40 to pump eluant from eluant reservoir 50. Under the operation of controller 80, pump 40 can pump eluant from eluant reservoir 50 through radioisotope generator 52, and thereby generate the radioactive eluate via elution through the generator. In different examples, pump 40 may pump eluate at a constant flow rate or a flowrate that varies over time. In some examples, pump 40 pumps eluant at a rate ranging from 5 milliliters/minute to 100 mL/minute, such as a rate ranging from 10 mL/minute to 85 mL/minute, or a rate ranging from 25 mL/minute to 75 mL/minute. Radioactive eluate generated typically flows at the same rate as the rate at which pump 40 pumps eluant.

As eluant flows through radioisotope generator 52, a radioactive decay product of a parents radioisotope bound in the generator may release and enter the flowing eluant, thereby generating the radioactive eluate. The type of eluant used may be selected based on the characteristics of the parent radioisotope and support material used for radioisotope generator 52. Example eluants that may be used include aqueous-based liquids such as saline (e.g., 0.1-1 M NaCl). For example, in the case of a strontium-rubidium radioisotope generator, a Normal (isotonic) saline may be used as an eluant to elute Rb-82 that has decayed from Sr-82 bound on a support material.

Radioactive eluate generated by radioisotope generator 52 can be conveyed to beta detector 58, allowing the radioactivity level (also referred to as activity) of the eluate to be determined based on measurements made by the beta detector (204). In some configurations, radioactive eluate is supplied to tubing or a reservoir positioned proximate to beta detector 58, allowing the beta detector to measure beta emissions emanating from a stopped and static volume of fluid positioned in front of the detector. In other configurations, beta detector 58 can detect beta emissions emanating from radioactive eluate flowing through tubing positioned proximate to the detector. For example, beta detector 58 may detect beta emissions emanating from radioactive eluate as the eluate flows through radioisotope generator discharge line 75 to waste container 54. Controller 80 may receive a signal from beta detector 58 indicative of the beta emissions measured by the beta detector.

Controller 80 may determine the activity of the radioactive eluate based on the beta emissions measured by beta detector 58. For example, controller 80 may compare a magnitude of the beta emissions measured by beta detector 58 to calibration information stored in memory relating different beta emission levels to different radioactive eluate activity levels. Controller 80 can then determine the activity of the radioactive eluate with reference to the calibration information and the beta emissions measured by beta detector 58 for the current radioactive eluate flowing through radioisotope generator discharge line 75. With all measurements made by system 10, controller 80 may account for radioactive decay between the radioisotope generator and a respective detector as the radioactive eluate travels through one or more tubing lines, or one detector and another detector and/or a patient and/or eluate-receiving container (e.g., from first measurement to delivery or subsequent measurement).

Because beta emissions from different radioisotopes are not easily distinguishable from each other, controller 80 may not be able to resolve what portion of the measured activity is attributable to one radioisotope as opposed to one or more other radioisotopes that may be present in the radioactive eluate. In instances where the radioactive decay product present in the radioactive eluate is assumed to be the predominant radioisotope species, controller 80 may set the measured activity of the radioactive eluate as the activity corresponding to the radioactive decay product. For example, in the case of a strontium rubidium radioisotope generator, the activity of radioactive eluate determined using beta detector 58 may be assumed to be the activity of Rb-82 present in the radioactive eluate. This is because the activity of any other radioisotopes that are present in the radioactive eluate may be assumed to be significantly (e.g., orders of magnitude) smaller than the activity of Rb-82 present in the radioactive eluate.

In some examples, pump 40 continuously pumps eluant through radioisotope generator and radioactive eluate is delivered to waste container 54 until the activity level of the radioactive eluate reaches a threshold level. Radioactive eluate generated by radioisotope generator 52 after the generator has been inactive for a period of time may initially have a lower activity than radioactive eluate generated during continued elution of the generator. For example, the activity of bolus radioactive eluate produced using generator 52 may follow an activity curve that varies based on the volume of eluant passed through the generator and the time since the start of the elution. As additional eluant is flowed through the radioisotope generator and time progresses, the activity may decrease from the peak activity to an equilibrium.

In some examples, radioactive eluate generated by radioisotope generator 52 is supplied to waste container 54 until the radioactive eluate reaches a minimum threshold activity value. The minimum threshold activity value can be stored in a memory associated with controller 80. In operation, controller 80 can compare the current activity of the radioactive eluate produced using generator 52 to the activity stored in memory (206). Controller 80 may determine when to actuate second multi-way valve 74 to direct radioactive eluate from waste container 54 to infusion tubing 70, and correspondingly patient line 72, based on the comparison (208).

Since the peak activity of radioactive eluate generated by radioisotope generator 52 may vary over the service life of the generator, the minimum activity threshold may be set relative to one or more previous elution/infusion procedures performed by the radioisotope generator system. For example, for each elution performed by system 10, controller 80 may store in a memory associated with the controller a peak radioactivity detected during that elution, e.g., as measured via beta detector 58. During a subsequent elution, controller 80 may reference the peak radioactivity, which may also be considered a maximum radioactivity, measured during a prior elution. Controller 80 may use that maximum radioactivity from the prior run as a threshold for controlling the radioisotope generator during the subsequent run. In some examples, the threshold is a percentage of the maximum radioactivity measured during a prior elution run, such as an immediate prior elution run. The immediate prior elution run may be the elution run performed before the current elution run being controlled without any intervening elution having been performed between the two evolutions. For example, the threshold may be an activity value falling within a range from 5% to 15% of the magnitude of maximum radioactivity detected during a prior elution run, such as from 8% to 12% of the magnitude of maximum activity, or approximately 10% of the magnitude of the maximum activity. In other examples, the threshold may not be determined based on a prior radioactivity measurement measured using system 10 but may instead be a value stored in a memory associated with controller 80. The value may be set by a facility in charge of system 10, the manufacturer of system 10, or yet other party with control over system 10.

In the example of FIG. 3, controller 80 controls second multi-way valve 74 to divert radioactive eluate from waste container 54 to the patient via infusion tubing 70 and patient line 72 connected to the infusion tubing (210). Upon determining that the activity of radioactive eluate flowing through radioisotope generator discharge line 75 via beta detector 58 has reached the threshold (e.g., equals or exceeds the threshold), controller 80 may control second multi-way valve 74 (e.g., by controlling an actuator associated with the valve) to deliver the radioactive eluate to the patient. Pump 40 may continue pumping the eluant through radioisotope generator 52, thereby delivering radioactive eluate to the patient, until a desired amount of radioactive eluate has been delivered to the patient.

In some examples, the desired amount of radioactive eluate is a set volume of eluate programmed to be delivered to the patient. Controller 80 can determine the volume of radioactive eluate delivered to the patient, e.g., based on knowledge of the rate at which pump 40 pumps and the duration the pump has pumped radioactive eluate. Additionally or alternatively, system 10 may include one or more flow sensors providing measurements to controller 80 concerning the volume of eluant and/or volume of radioactive eluate flowing through one or more tubing lines of the system.

In some examples, controller 80 tracks the cumulative volume of radioactive eluate generated by radioisotope generator 52, e.g., from the time at which the generator is installed in the system 10. Controller 80 may track the volume of radioactive eluate generated during patient infusion procedures as well as other modes of operation where radioactive eluate is generated but may not be supplied to a patient, e.g., during QC testing. In some examples, controller 80 compares the cumulative volume of radioactive eluate generated by radioisotope generator 52 to an allowable limit and prevents at least any further patient infusion of radioactive eluate using the generator when the cumulative volume is determined to exceed (e.g., be equal to or greater than) the allowable limit. In these configurations, the cumulative volume delivered by the radioisotope generator can act as a control point for determining when the generator should be taken out of service. While the allowable limit can vary based on a variety of factors such as the size and capacity of the radioisotope generator, in some examples, the allowable limit is less than 250 L, such as less than 150 L, less than 100 L, less than 50 L, or less than 25 L. For example, the allowable limit may range from 5 L to 100 L, such as from 10 L to 60 L, from 15 L to 40 L, or from 17 L to 30 L. In one particular example, the allowable limit is 17 L. In another particular example, the allowable limit is 30 L. System 10 can have hardware and/or software locks that engage to prevent a subsequent patient infusion procedure once the allowable limit is reached. For example, controller 80 may prevent pump 40 from pumping eluant once the allowable limit has been exceeded.

In addition to or in lieu of controlling the desired amount of radioactive eluate based on the volume of eluate delivered to the patient, controller 80 may control the desired amount of radioactive eluate based on the cumulative amount of radioactivity delivered to the patient (e.g., adjusting for radioactive decay during delivery). Controller 80 may control pump 40 to deliver eluant to radioisotope generator 52, thereby delivering radioactive eluate to the patient, until the cumulative amount of radioactivity delivered to the patient reaches a set limit. Controller 80 can determine the cumulative amount of radioactivity delivered to the patient by measuring the activity of the radioactive eluate via beta detector 58 during the delivery of the radioactive eluate to the patient. When controller 80 determines that the set amount of radioactivity has been delivered to the patient, controller 80 may control pump 40 to cease pumping the eluant and/or control one or more valves in system 10 to redirect flow through the system.

In some examples, controller 80 controls first multi-way valve 64 to redirect eluant flowing through system 10 from radioisotope generator inlet line 66 to bypass line 68. Controller 80 may or may not control second multi-way valve 74 to place radioisotope generator discharge line 75 in fluid communication with the waste line 76 instead of infusion tubing line 70. Controller 80 may control pump 40 to pump eluant through bypass line 68 into infusion tubing 70 and patient line 72. Controller 80 may control the pump to pump a volume of eluant through the lines sufficient to flush residual radioactive eluate present in the lines from the lines into the patient. This may help remove residual sources of radioactivity from the environment surrounding the patient which may otherwise act as interference during subsequent diagnostic imaging. Independent of whether controller 80 controls system 10 to provide an eluant flush following delivery of radioactive eluate to the patient, controller 80 can terminate operation of pump 40 to terminate the patient infusion procedure (212).

As noted above, system 10 may be used to generate and deliver radioactive eluate in other applications in which infusion tubing 70 is not connected to a patient. As one example, system 10 may generate radioactive eluate that is subject to quality control evaluation during a quality control mode of operation. During the quality control mode of operation, radioactive eluate produced by system 10 may be analyzed to determine the radioactivity of one or more species of radioisotopes present in the radioactive eluate. In practice, when eluant is passed through a radioisotope generator containing a parent radioisotope bound on a support material, a daughter decay product radioisotope that binds less tightly to the support material than the parent radioisotope can release into the eluant to form the radioactive eluate. One or more other radioisotopes besides the daughter decay product intended to be eluted into the eluant may also enter the liquid. Periodic quality control evaluation of the radioactive eluate may be performed to determine the activity level of these one or more other radioisotopes to help ensure that the activity level does not exceed a determine limit.

For example, in the case of a strontium-rubidium radioisotope generator, when eluant is passed through the generator, Rb-82 may be generated as a radioactive decay product from Sr-82 contained in the radioisotope generator, thereby generating the radioactive eluate. The eluate may contain radioisotopes besides Rb-82, with the number and magnitude of the radioisotopes varying, e.g., based on the operational performance of the generator. For example, as the generator is used to generate doses of Rb-82, Sr-82 and/or Sr-85 may release from the generator and also enter the eluate. As another example, cesium-131 may enter the eluate in trace amounts. Accordingly, the total amount of radioactivity measured from the radioactive eluate may not be attributable to one particular radioisotope but may instead be the sum amount of radioactivity emitted by each of the different radioisotopes present in the eluate.

Figure 4:
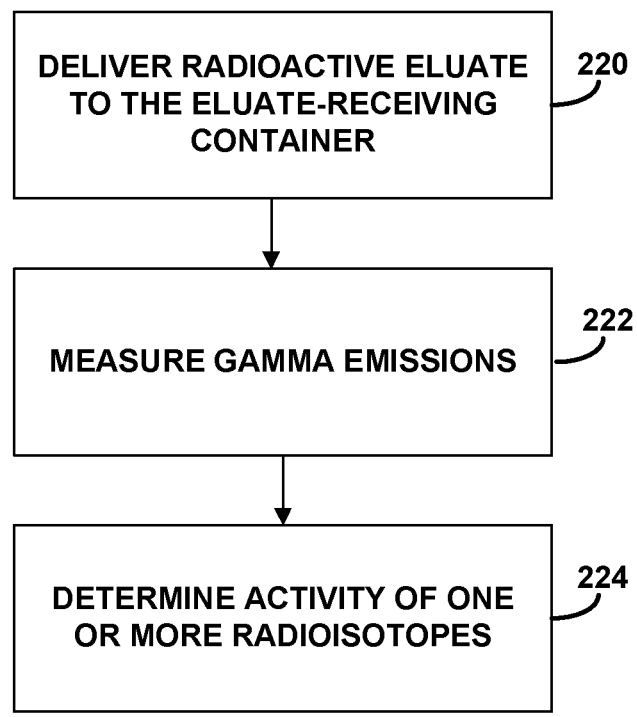
FIG. 4 is a flow diagram of an example technique that may be used to perform a quality control procedure to measure an activity of one or more radioisotopes.

During quality control evaluation, the activity of one or more radioisotopes present in the radioactive eluate (e.g., in addition to or in lieu of the decay product targeted for generation by the radioisotope generator) may be determined and compared to one or more allowable thresholds. FIG. 4 is a flow diagram of an example technique that may be used to perform a quality control procedure. For example, the technique of FIG. 4 may be used by system 10 to help ensure that radioactive eluate generated by radioisotope generator 52 meets the standards set for patient infusion. As with FIG. 3, the technique of FIG. 4 will be described with respect to system 10, and more particularly the arrangement of exemplary components described with respect to FIG. 1 above, for purposes of illustration. However, it should be appreciated that the technique may be performed by systems having other arrangements of components and configurations, as described herein.

In the technique of FIG. 4, controller 80 can control system 10 to deliver radioactive eluate to the eluate-receiving container 56 positioned proximate to a gamma detector 60 (220). To initiate the process, an operator may insert a terminal end of infusion tubing line 70 into eluate-receiving container 56 for collecting a sample of eluate (e.g., for evaluation by gamma detector 60 and/or dose calibrator 84). With infusion tubing line 70 in fluid communication with eluate-receiving container 56, the resulting arrangement may place radioisotope generator 52 in fluid communication with the eluate-receiving container via second multi-way valve 74. That is, when arranged to perform a quality control elution, the outlet of infusion tubing 70 can be placed in communication with eluate-receiving container 56 and not in communication with patient line 72 or any patient connected to the patient line. When so arranged, radioactive eluate generated by radioisotope generator 52 can be supplied to eluate-receiving container 56 for evaluation by gamma detector 60 instead of being delivered to a patient during a patient infusion procedure.

Once system 10 is suitably arranged to allow eluate-receiving container 56 to receive radioactive eluate from radioisotope generator 52, controller 80 can control the system to generate radioactive eluate that is supplied to the eluate-receiving container. In some examples, controller 80 initiates a quality control elution in response to instructions received via user interface 16 by an operator to perform the quality control elution. For example, controller 80 may execute software that guides the operator through one or more steps to appropriately arrange the components of system 10 for the quality control elution and receives feedback (e.g., via sensors and/or the operator via the user interface) confirming that the components are appropriately arranged before generating radioactive eluate. Controller 80 can control system 10 to execute the quality control elution immediately after arranging the components of system 10 to perform the elution or at a delayed time after the components have been arranged for the quality control elution.

In instances where the quality control procedure takes a comparatively long time to execute, for example, an operator may set system 10 to perform a quality control elution at a time when the system is not typically used for patient infusion procedures. For example, system 10 may be set to perform a quality control procedure at a preset time in the day, such as over the midnight hour or in the evening. As examples, system may be set to perform the quality control elution at a time between 5 PM in the evening and 7 AM the next day, such as between 8 PM in the evening and 6 AM the next day, or between 12 AM and 8 AM the next day (e.g., between 12 AM and 4 AM) in the time zone where the system is located. The operator may install eluate-receiving container 56 and/or tubing and place the eluate-receiving container in fluid communication with the tubing prior to leaving the system unattended. Thereafter, system 10 operating under the control of controller 80 may execute the quality control procedure at a subsequent preprogrammed time. The quality control results may then be available to the operator when they return to the system.

Regardless of the time at which system 10 executes the quality control elution, controller 80 can control pump 40 to pump eluant through radioisotope generator 52, thereby generating the radioactive eluate that is supplied to the eluate-receiving container. In some examples, radioactive eluate generated by radioisotope generator 52 is supplied directly to eluate-receiving container 56 via infusion tubing 70 without diverting an initial portion of the radioactive eluate to waste container 54. In other examples, radioactive eluate generated by radioisotope generator 52 is initially directed to waste container 54 until a threshold level of activity is reached as determined via beta detector 58. Upon determining that radioactive eluate being generated by radioisotope generator 52 has reached a threshold level of activity, controller 80 can control second multi-way valve 74 to direct radioactive eluate flowing from radioisotope generator discharge line 75 to infusion tubing 70 (and eluate-receiving container 56 connected thereto) instead of to waste container 54.

For example, controller 80 may follow steps 200-208 discussed above with respect to FIG. 3 during a quality control elution to supply radioactive eluate to eluate-receiving container 56. Controller 80 can divert radioactive eluate initially generated by radioisotope generator 52 to waste container 54 until the activity of the radioactive eluate as determined via beta emissions measured by beta detector 58 reaches a threshold. Upon the activity of radioactive eluate generated by radioisotope generator 52 reaching the threshold, controller 80 can control multi-way valve 74 to direct the radioactive eluate to eluate-receiving container 56.

Pump 40 can continue supplying eluant to radioisotope generator 52 and thereby supply radioactive eluate to eluate-receiving container 56 until a desired amount of radioactive eluate is supplied to the container. In some examples, the desired amount of radioactive eluate is a pre-established volume of radioactive eluate, e.g., based on the size of eluate-receiving container 56. Controller 80 can control pump 40 to supply an amount of radioactive eluate to eluate-receiving container 56 sufficient to at least partially, and in some cases fully, fill the eluate-receiving container with radioactive eluate. In some embodiments, eluate-receiving container 56 may be filled to greater than 50% of its maximum volume with radioactive eluate, such as from 50% to 100% of its maximum volume, greater than 75% of its maximum volume, or from 60% to 90% of its maximum volume. The total volume to which eluate-receiving container 56 is filled during a quality control procedure, which may be referred to as a quality control (QC) threshold volume may be greater than 5 mL, such as from 5 mL to 100 mL or from 5 mL to 50 mL. As examples, the QC threshold volume may range from 10 mL to 20 mL, from 20 mL to 30 mL, from 30 mL to 40 mL, from 40 mL to 50 mL, from 50 mL to 75 mL, or from 75 mL to 100 mL. For example, in one specification application, the QC threshold volume is about 50 mL.

In addition to or in lieu of controlling the amount of radioactive eluate supplied to eluate-receiving container 56 based on volume, controller 80 may control the amount of radioactive eluate supplied to the container based on activity measurements made by beta detector 58. As radioactive eluate flows past the beta detector 58 to eluate-receiving container 56, the beta detector can measure the beta emissions emitted by the radioactive eluate. Controller 80 can receive a signal from beta detector 58 indicative of the beta emissions measured by beta detector 58 and may compare a magnitude of the beta emissions measured by the beta detector to calibration information stored in memory relating different beta emission levels to different radioactive eluate activity levels. Controller 80 may determine a cumulative amount of activity delivered to eluate-receiving container 56 based on the activity of the radioactive eluate measured by the beta detector and/or the flow rate of the radioactive eluate (e.g., adjusting for radioactive decay during delivery). Controller 80 can compare the cumulative amount of activity delivered to eluate-receiving container 56, which may be referred to as an accumulated radioactive dose supplied to the container, to one or more thresholds stored in a memory associated with the controller.

For example, controller 80 may compare the cumulative amount of activity supplied to eluate-receiving container 56 to a quality control (QC) threshold level stored in a memory associated with the controller. The QC threshold level may be programmed, e.g., by an operator or manufacturer of system 10. In some examples, the QC threshold level is greater than 5 mCi, such as greater than 15 mCi. For example, the QC threshold level may range from 5 mCi to 75 mCi, such as from 10 mCi to 60 mCi, from 15 mCi to 50 mCi, or from 20 mCi to 40 mCi. In one specific example, the threshold QC level is approximately 30 mCi. The threshold QC level can be the total activity of the radioactive eluate supplied to eluate-receiving container 56 as measured by beta detector 58 and as corrected for radioactive decay during delivery based on time and half-life. Where a single radioisotope is assumed to be the dominant source of radioactivity, the threshold level may be assumed to correspond to that radioisotope. In the example of a strontium-rubidium radioisotope generator where Rb-82 is expected to be the dominant source of activity in the radioactive eluate flowing past the beta detector 58, the threshold QC level activity may be designated as a threshold QC level of Rb-82.

Upon determining that the accumulated radioactive dose of radioactive eluate supplied to eluate-receiving container 56 has reached the QC threshold level, controller 80 can control pump 40 to cease pumping eluant through radioisotope generator 52. Accordingly, in these examples, the amount of activity delivered to eluate-receiving container 56 can act as a control point for determining how much volume of radioactive eluate to deliver to the container. Controller 80 may also monitor the volume of radioactive eluate delivered to eluate-receiving container 56 and control pump 40 to cease pumping if the eluate-receiving container will exceed its maximum capacity, even if the QC threshold level has not been reached. In these circumstances, controller 80 may issue a user alert via user interface 16 indicating an issue with the quality control testing.

In the technique of FIG. 3, gamma detector 60 measures gamma emissions emitted by radioactive eluate supplied to eluate-receiving container 56 (220). Gamma detector 60 can continuously measure gamma emissions, e.g., during filling of eluate-receiving container 56 and/or after the eluate-receiving container has suitably filled with radioactive eluate. Alternatively, gamma detector 60 may periodically sample gamma emissions, e.g., at one or more times after eluate-receiving container 56 has suitably filled with radioactive eluate. In other implementations of the technique of FIG. 3 using dose calibrator 84 instead of gamma detector 60, the activity of one or more radioisotopes of interest can be measured using the dose calibrator instead of the gamma detector.

However, in examples where gamma detector 60 is used, the gamma detector can measure gamma emissions emanating from radioactive eluate in eluate-receiving container 56 at least upon the container being initially filled when the pump stopped pumping radioactive eluate to the container. Gamma detector 60 can measure gamma emissions emanating from radioactive eluate in eluate-receiving container at one or more times after the container has filled with radioactive eluate, in addition to or in lieu of measuring the gamma emissions upon the container being initially filled. For example, gamma detector 60 may measure gamma emissions emanating from radioactive eluate in eluate-receiving container 56 after a period of time sufficient for substantially all the initial daughter radioisotope (e.g., Rb-82) in the radioactive eluate to decay.

In some examples, the period of time sufficient for substantially all the initial daughter radioisotope to decay is at least 3 half-lives of the daughter radioisotope, such as at least 5 half-lives of the daughter radioisotope. In the case of Rb-82 which has a half-life of about 76 seconds, the period of time may be greater than 15 minutes, such as greater than 20 minutes, or greater than 30 minutes. For example, the period of time may range from 15 minutes to one hour, such as 25 minutes to 45 minutes. Controller 80 can control gamma detector 60 to measure gamma emissions emanating from radioactive eluate in the eluate-receiving container 56 after the period of time has passed from the filling of the eluate-receiving container. As noted above, gamma detector 60 may or may not continuously measure gamma emissions emanating from the radioactive eluate both before and after the period of time has passed.

The gamma emission energies measured by gamma detector 60 may vary depending on the type of radioisotope generator utilized for radioisotope generator 52 and, correspondingly, the gamma emission energies of specific radioisotopes produced by the generator. In some examples, gamma detector 60 is implemented as a wide range detector that detects a large gamma spectrum. In other examples, gamma detector is implemented as a narrow range detector or is windowed to detect a comparatively narrower gamma spectrum.

In some applications, such as when radioisotope generator 52 is implemented as a strontium-rubidium radioisotope generator, gamma detector 60 may be configured to measure gamma emissions at least in a range from 400 kilo-electron volts (keV) to 800 keV, such as from 400 keV to 776 keV, from 450 keV to 550 keV, from 465 keV to 537 keV, or from 511 keV to 514 keV. In some examples, gamma detector 60 measures gamma emissions at least at a gamma emission energy of 511 keV and/or 514 keV. In general, the gamma emission energy ranges detected by gamma detector 60 may be set depending on the gamma emission energies of one or more radioisotopes of interest for measurement.

Figure 9:
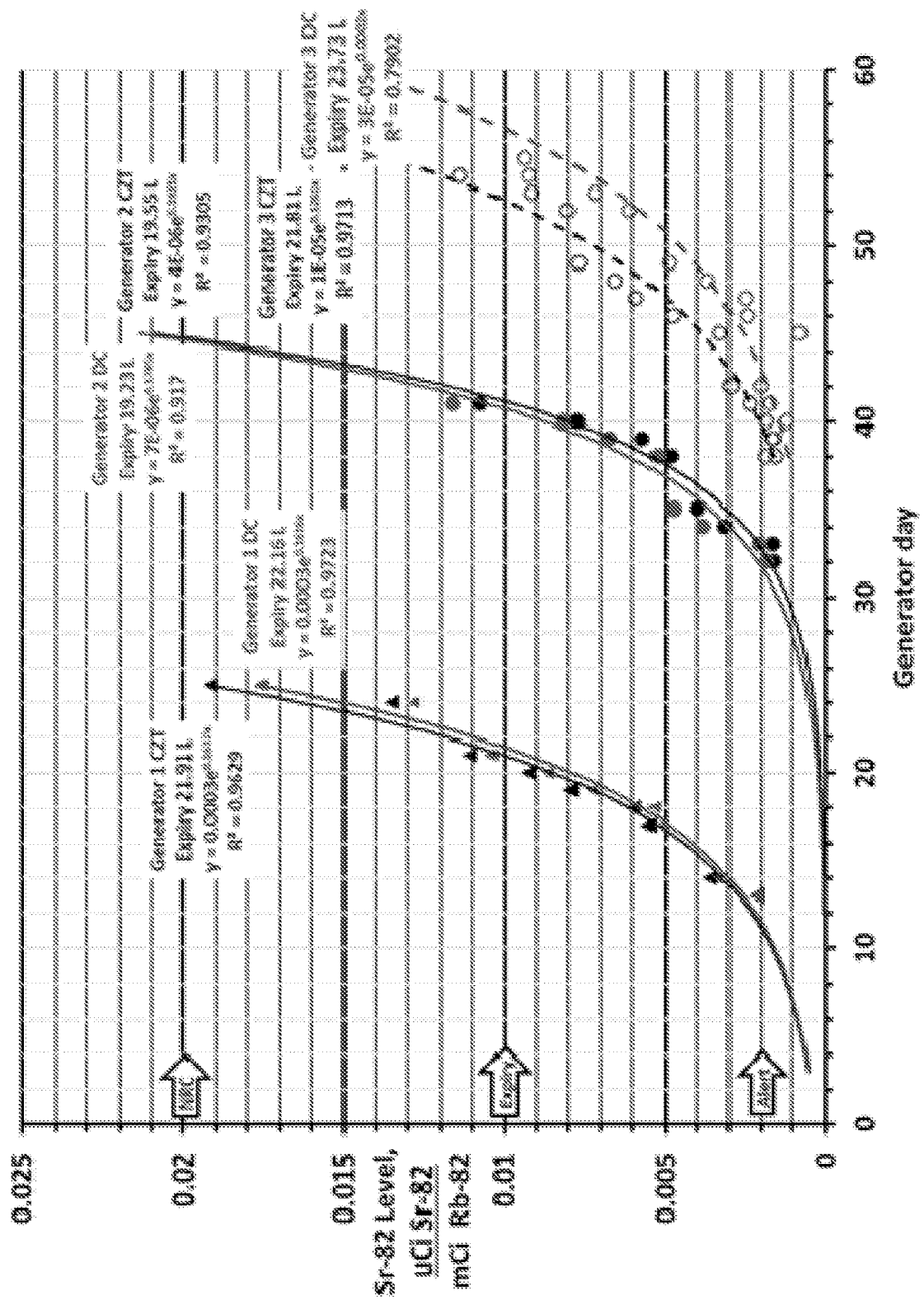
FIG. 9 is a plot of actual Sr-82 µCi data as a function of eluated volume as illustrated in days of operation.

Gamma detector 60 can send, and controller 80 can receive, a signal indicative of the gamma emissions measured by the gamma detector. In the technique of FIG. 9, controller 80 determines the presence and/or activity of one or more radioisotopes present in the radioactive eluate based on the measured gamma emissions (224). Controller 80 may determine the amount of activity associated with a particular energy line of the gamma spectrum which corresponds to a particular radioisotope, thereby determining the activity of that radioisotope.

In general, activity may be reported in Becquerel (Bq) or Curie (Ci) and is a function of the composition of a particular radioisotope and the amount of the radioisotope in the radioactive eluate. To determine the amount of activity associated with a particular radioisotope, controller 80 may identify a region of interest of the gamma spectrum encompassing the energy line corresponding to that radioisotope and integrate the area under the peak for that energy line. The region of interest may be a region defined between two different energy lines that includes the peak of interest and bounds the region under which the peak area is integrated to determine corresponding activity.

In the case of a strontium-rubidium radioisotope generator, controller 80 may determine an activity of Sr-82 and/or Sr-85 and/or any other desired radioisotopes of interest. In some examples, controller 80 can determine an activity of Sr-82 by determining an activity associated with the 511 keV line of the gamma spectrum. In general, the activity of Sr-82 may not be measured directly via gamma emissions but may be measured by measuring the activity of Rb-82, which is the decay product of Sr-82 and can emit gamma emissions at the 511 keV energy line. In instances where the gamma spectrum is measured after a period of time sufficient for substantially all initial Rb-82 present in the radioactive eluate supplied from radioisotope generator 52 to decay, Rb-82 emissions measured at the 511 keV energy line may be assumed to be Rb-82 decayed from Sr-82 present in the radioactive eluate, thereby providing a measurement of the Sr-82 activity. Controller 80 can determine the net peak integral count in the region of interest encompassing the 511 keV line to determine the activity of Sr-82. Controller 80 may then store the determined activity of Sr-82 in a memory associated with the controller.

As another example, controller 80 can determine an activity of Sr-85 by determining an activity associated with the 514 keV line of the gamma spectrum. Controller 80 can determine the net peak integral count in the region of interest encompassing the 514 keV line to determine the activity of Sr-85. Controller 80 may then store the determined activity of Sr-85 in a memory associated with the controller.

In applications where both the activity of Sr-82 and Sr-85 are determined, controller can determine the respective activity of each radioisotope by gamma spectrum analysis as discussed above. Alternatively, controller 80 may determine the activity of one of Sr-82 or Sr-85 by gamma spectrum analysis as discussed above and determine the activity of the other strontium radioisotope with reference to a ratio stored in memory relating the activity of Sr-82 to the activity of Sr-85. The activity of Sr-82 may be related to the activity of strontinum-85 by a known radioisotope ratio, which may be stored in memory associated with controller 80. Controller 80 can determine the activity of one radioisotope by multiplying the determined activity of the other radioisotope by the stored ratio. In some examples, controller 80 sums the determined activity of Sr-82 and the determined activity of Sr-85 to identify the total strontium activity in the radioactive eluate.

If desired, controller 80 can identify the amount of activity associated with other radioisotopes in the radioactive eluate based on the gamma emission data received from gamma detector 60. Controller 80 can identify region(s) of interest encompassing other gamma emission energy lines corresponding to the radioisotopes and determine a net peak integral count for each energy line. Each energy line may correspond to a particular radioisotope, and the correspondence between different energy lines and different radioisotopes may be stored in a memory associated with the controller. Additional details on gamma detector arrangements and gamma emission processing can be found in U.S. Pat. No. 9,766,351, entitled "REAL TIME NUCLEAR ISOTOPE DETECTION," the entire contents of which are incorporated herein by reference.

Activity measurements made for one or more radioisotopes in the radioactive eluate can be stored and/or used for variety of purposes in radioisotope generator system 10. For example, the activity of one more radioisotopes of interest may be tracked and stored by controller 80 for determine a predicted volume at which the radioisotope will exceed a threshold during subsequent operation.

Figure 5:
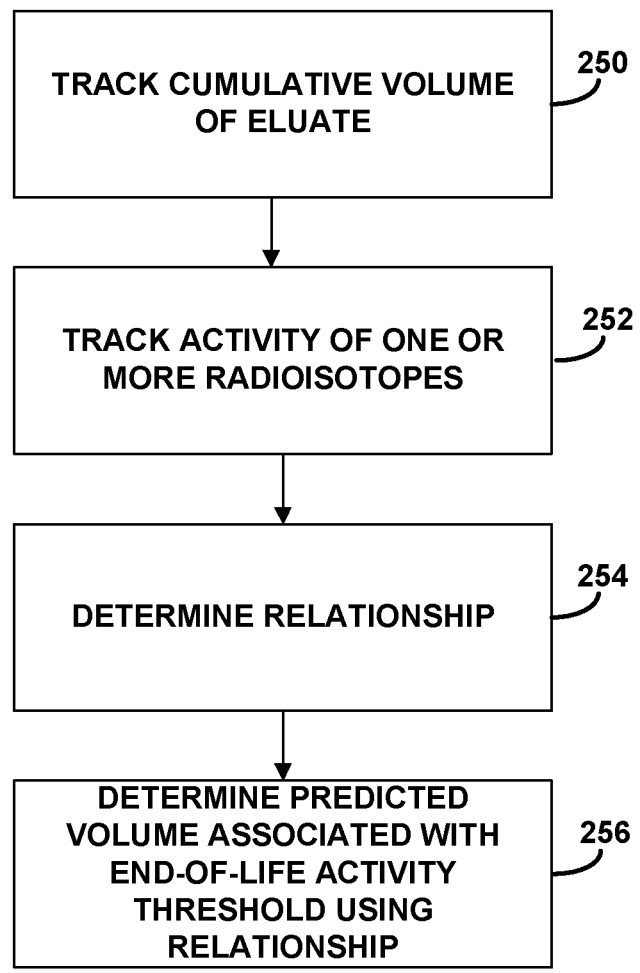
FIG. 5 is a flow diagram of an example technique for determining a predicted volume of eluate produced by a radioisotope generator at which the activity of a radioisotope of interest will reach a threshold.

FIG. 5 is a flow diagram of an example technique for determining a predicted volume of eluate produced by a radioisotope generator at which the activity of a radioisotope of interest will reach a threshold. In the technique of FIG. 5, controller 80 tracks the cumulative volume of eluate produced by radioisotope generator 52 (250). Controller 80 may track the cumulative volume by storing one or more values indicative of the volume of eluate produced by the generator in a non-transitory computer readable memory associated with the controller. Controller 80 may track the cumulative volume by generating a sum or total volume of eluate generated by radioisotope generator 52 from a plurality of individual volumes generated by the radioisotope generator and measured. Since individual volumes generated by radioisotope generator 52 and measured (e.g., tracked) may include all eluant delivered to the generator (and, correspondingly all eluate discharging from the generator), including when the eluate is delivered to a patient, waste reservoir 54, and to eluate-receiving container 56 through multiple runs following installation in system 10. The cumulative volume may be stored in the form of one or more values, and may be stored in a table or other data structure usable by controller 80. Controller 80 may track the cumulative volume eluate produced by radioisotope generator 52 by storing one or more values indicative of the volume of eluate produced by the generator each time eluate is produced by the generator.

Controller 80 may receive the information from one or more communicatively connected components such as a flow rate sensor monitoring a flow rate of eluant pumped through generator 52 (and/or eluate produced from the generator), a displacement sensor monitoring a position of pump 40 (and hence the corresponding volume expected to be delivered by the pump based on position), a sensor monitoring an amount of electrical power (e.g., current) drawn by pump 40 during operation (and hence the corresponding volume expected to be delivered by the pump based on the power), and/or other feature corresponding to the volume of eluate produced by radioisotope generator 52.

The technique of FIG. 5 also includes tracking an activity of an radioisotope of interest, such as a first radioisotope different than a second radioisotope intended for injection into a patient undergoing a clinical procedure using system 10 (252). In some examples, the first radioisotope is a parent radioisotope and the second radioisotope is a daughter radioisotope (e.g., decay product of the first radioisotope). In either case, controller 80 may track the activity of the one or more radioisotopes of interest as measured during the quality control procedure using gamma detector 60 (FIG. 1) and/or dose calibrator 84 (FIG. 2). For example, controller 80 may track the activity of the radioisotope by storing a value indicative of the activity in a non-transitory computer readable memory associated with the controller. The activity may be stored in the form of one or more values, and may be stored in a table or other data structure usable by controller 80. Controller 80 may track the activity of the one or more radioisotopes of interest by storing a value indicative of the activity determined during each quality control procedure (for example as discussed above with respect to FIG. 4) performed since the beginning of the service life of the generator (e.g., the generator is newly filled or refilled and installed in system 10). Alternatively, controller 80 may track the activity of the one or more radioisotopes of interest by storing a value indicative of the activity determined during each quality control procedure after a threshold amount of eluate has been generated by the system, such as at least 100 ml, at least 500 ml, at least 1 liter, or at least 2 liters.

The technique of FIG. 5 also includes determining a relationship between the tracked cumulative volume and the tracked activity (254). Controller 80 can analyze the tracked cumulative volume of the radioactive eluate produced by radioisotope generator 52 and the tracked activity of the first radioisotope and determine a relationship between the tracked volume and tracked activity. For example, controller 80 may perform a curve fitting process such as a regression analysis to determine a relationship between the tracked volume and the tracked activity. The determined relationship (or coefficients associated therewith) can then be stored in a memory associated with the controller.

In some examples, controller 80 may fit a curve representing tracked activity plotted on a y-axis of a graph with corresponding cumulative volume data plotted on the x-axis of the graph. Controller 80 may fit a first order curve having a slope and an intercept or a higher order curve (e.g., second order, third order, or higher), with additional coefficients corresponding to the higher order curve. The curve and/or coefficients thereof may be stored in memory. Controller 80 may employ any suitable statistical software package such as, e.g., Minitab, Excel, or the like, to generate the relationship.

The technique of FIG. 5 also involves determining a predicted volume of radioactive eluate generated by the radioisotope generator at which the activity of the first radioisotope in the radioactive eluate will reach a threshold (256). Controller 80 may extrapolate the determined relationship from a current cumulative volume of eluate produced by radioisotope generator 52 to a volume at which the corresponding activity of the first radioisotope will be at a threshold. The volume at this extrapolation can be deemed the predicted volume at which the activity of the undesired radioisotope in the radioactive eluate will reach the threshold.

In the case of a Sr-82/Rb-82 radioisotope generator that produces radioactive rubidium-82 from a radioisotope generator containing strontium-82, the threshold may be a Sr-82 level of less than 0.05 µCi per millicurie of Rb-82, such as less than 0.02 µCi per millicurie of Rb-82, about 0.02 µCi per millicurie of Rb-82, less than 0.01 µCi per millicurie of Rb-82, or about 0.01 µCi per millicurie of Rb-82. For example, the threshold may be a strontium-82 activity less than 0.02 µCi, such as a strontium-82 activity between 0.002 µCi and 0.02 µCi, or a strontium-82 activity of 0.01. Additionally or alternatively, the threshold may be a Sr-85 level of 0.5 µCi per millicurie of Rb-82, such as less than 0.2 µCi per millicurie of Rb-82, about 0.2 µCi per millicurie of Rb-82, less than 0.1 µCi per millicurie of Rb-82, or about 0.1 µCi per millicurie of Rb-82. Any threshold may be stored in a memory associated with controller 80.

In some examples, controller 80 is configured to determine the predicted volume a plurality of times, each time (or at a lesser frequency) in response to receiving new data concerning the cumulative volume of radioactive eluate generated by radioisotope generator 52 and/or the activity of an undesired radioisotope in the radioactive eluate generated by the radioisotope generator. As new tracked volume and activity data is received by controller 80 longer in the service life of radioisotope generator 52, controller 80 may be able to refine and determine the predicted volume with increasing accuracy.

It should be appreciated that while the foregoing tracking and determination of the predicted volume in conjunction with FIG. 5 are described as being performed by controller 80, the computing functionality attributed to controller 80 in system 10 may be performed on any one or more controllers associated with the system, be it physically on system 10 or remotely located, and the functionalities described herein are not limited to being performed on any specific hardware device.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), magnetoresistive random access memory (MRAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

The following examples may provide additional details about radioisotope delivery systems in accordance with the disclosure.

Example 1

Sr-82 and Sr-85 samples covering the range of activity levels that may be observed during operation of a strontium-rubidium radioisotope generator were compared using three exemplary measurement systems: a CZT gamma detector, a dose Calibrator, and a high-purity germanium gamma detector (HPGe). Twelve activity readings were made across the range of activity levels for each of the detectors. The results are presented in Table 1 below.

TABLE 1

Comparison of measurements by the three detector systems

| | HPGe Gamma Detector | | | | Sr-82 Level # Ratio µCi/ mCi Rb-82 | CZT Gamma Detector | | | | Dose Calibrator | | | |
|---|---|---|---|---|---|---|---|---|---|---|---|---|---|
| | Sr-82 | | Sr-85 | | | Sr-82 | | | Sr-85 | Reading | Sr-82 | | Sr-85 |
| ID | µCi | % CV** | µCi | % CV | | µCi | Error %* | % CV** | µCi | µCi | µCi | % Error* | µCi |
| 1 | 7.0488 | 0.5 | 10.4061 | 0.1 | 0.2350 | 6.211 | 11.89 | 0.31 | 9.080 | 11.19 | 6.58 | 6.71 | 9.61 |
| 2 | 3.4297 | 0.7 | 5.0836 | 0.2 | 0.1143 | 3.098 | 9.67 | 0.44 | 4.529 | 5.63 | 3.31 | 3.54 | 4.84 |
| 3 | 0.7642 | 1.5 | 1.1258 | 0.4 | 0.0255 | 0.709 | 7.26 | 0.93 | 1.037 | 1.25 | 0.73 | 3.92 | 1.07 |
| 4 | 0.4285 | 2.0 | 0.6219 | 0.5 | 0.0143 | 0.39 | 8.98 | 1.25 | 0.570 | 0.74 | 0.43 | −1.48 | 0.64 |
| 5 | 0.2450 | 2.6 | 0.3506 | 0.7 | 0.0082 | 0.223 | 8.98 | 1.64 | 0.326 | 0.38 | 0.22 | 8.86 | 0.33 |
| 6 | 0.1420 | 3.4 | 0.2085 | 0.8 | 0.0047 | 0.131 | 7.75 | 2.14 | 0.192 | 0.24 | 0.14 | 0.68 | 0.21 |
| 7 | 0.0791 | 4.6 | 0.1142 | 1.1 | 0.0026 | 0.069 | 12.77 | 2.91 | 0.101 | 0.11 | 0.06 | 18.28 | 0.09 |
| 8 | 0.0501 | 5.8 | 0.0735 | 1.4 | 0.0017 | 0.044 | 12.18 | 3.62 | 0.064 | 0.06 | 0.04 | 29.63 | 0.05 |
| 9 | 0.0280 | 5.9 | 0.0421 | 1.4 | 0.0009 | 0.027 | 3.50 | 4.51 | 0.039 | 0.03 | 0.02 | 37.00 | 0.03 |
| 10 | 0.0152 | 5.7 | 0.0240 | 1.3 | 0.0005 | 0.015 | 1.48 | 5.87 | 0.022 | 0.03 | 0.02 | −15.78 | 0.03 |
| 11 | 0.0110 | 5.5 | 0.0160 | 1.3 | 0.0004 | 0.009 | 18.43 | 6.97 | 0.013 | 0.01 | 0.01 | 46.74 | 0.01 |
| 12 | 0.0104 | 4.9 | 0.0104 | 1.4 | 0.0003 | 0.006 | 42.21 | 8.25 | 0.009 | 0.04 | 0.02 | −126.38 | 0.03 |

$${}^{**}CV = \left(\frac{\sqrt{\text{Net Counts}}}{\text{Net Counts}}\right) \times 100, \text{ \# Based on 30 mCi } Rb\text{-}82,$$

$${}^{*}\% \text{ Error} = \frac{(HPGE - DC \text{ or } CZT)}{HPGe} \times 100$$

The date in Table 1 were interpreted relative to three exemplary ratios or limits, designated an alert limit, and expiry limit, and a legal limit. For Sr-82, the values corresponding to these limits for purposes of the experiment 0.002, 0.01, and 0.02 µCi Sr-82 per mCi of Rb-82, respectively. For Sr-85, the values corresponding to these limits for purposes of the experiment were ten-fold higher than the Sr-82 limits, or 0.02, 0.1, and 0.2 µCi Sr-85 per mCi of Rb-82, respectively. The ten-fold increase corresponds to a maximum ratio of Sr-85/Sr-82 of 10.

Samples were measured with the CZT detector using a 600 second acquisition. Background radiation was measured before the samples and corrected automatically by the infusion system for each strontium activity calculation. The % CV for the CZT detector data (Sr-82/85) was determined based on net counts and was <4% down to and including the Alert Limit (0.002) or a total Sr-82/85 content of 0.1 µCi and still only approximately 8% at a ratio of 0.0003 almost 10-fold lower.

Counting times for the HPGe detector were adjusted to obtain good counting statistics with a maximum CV of approximately 6%. The Sr85/82 ratio of 1.462 corresponded approximately that of the example Sr/Rb generator used for the experiment at the end of its 42-day life starting from an initial ratio of <1. The higher proportion of Sr-85 leads to more counts than for Sr-82 and the lower CVs seen in Table 1.

For the dose calibrator, the reading of each sample was allowed to stabilize for approximately 30 second before recording the result.

The data show that both the dose calibrator and the CZT detector were able to accurately measure Sr82/85 radioactivity levels down to below the Expiry Limit (ratio 0.01). However, whereas the CZT detector still exhibited an acceptable error down to a ratio of 0.0004 the Dose Calibrator exhibited unacceptable error at 0.0017, just below the Alert Limit, under the experimental conditions used. Any apparent errors in the readings provided by the CZT detector were uniform down to the second lowest sample but all positive, which suggests good precision but inaccuracy due to insufficient calibration. The errors of the dose calibrator were larger at lower levels and both positive and negative, suggesting accuracy at higher levels but a lack of precision at lower levels.

The data show that the CZT detector made precise measurements down to radioactivity levels well below those encountered at the Alert Limit while the dose calibrator lacked precision at radioactivity levels at or lower than the Alert Limit. This is consistent with counting statistics (indicating that sufficient counts are being recorded to achieve a desired precision). A dose calibrator may have a limited measurement resolution of only 0.01 µCi. This is typically caused by the resolution of the display, which cause rounding or truncation errors. Independent of and additive to any inherent uncertainty in the measurement, the minimum change that can be registered with dose calibrators exhibiting such precision for a total Sr-82/85 dose of 0.06+0.01 µCi at the Alert Limit for 30 mCi Rb-82 is plus or minus 17%.

The data show that the CZT used in the example was more precise than the dose calibrator at Sr-82/85 levels encountered near the Alert Limit.

Example 2

A second example set following the details outlined in Example 1 above was evaluated to further understand the measurement capabilities of an example gamma detector at quantifying activity measurements. Sr-82 and Sr-85 samples covering the range of activity levels that may be observed during operation of a strontium-rubidium radioisotope generator were compared using three exemplary measurement systems: a CZT gamma detector, a dose Calibrator, and a high-purity germanium gamma detector (HPGe). Twelve activity readings were made across the range of activity levels for each of the detectors.

The samples were evaluated for both trueness and precision. ISO 5725 uses the terms "trueness" and "precision" to describe the accuracy of a measurement method. "Trueness" refers to the closeness of agreement between the arithmetic mean of a large number of test results and the true or accepted reference value. "Precision" refers to the closeness of agreement between test results. The general term "accuracy" is used in ISO 5725 to refer to both trueness and precision. The precision of the three measurement methods is recorded in tables 2 and 3 as the % CV of each measurement. Table 2 presents the results for the high-purity germanium gamma detector. Table 3 presents comparative data for a dose calibrator and an example CZT detector that may be implemented on a system according to the disclosure.

TABLE 2

Truth standard, HPGe data

| ID | Sr-82 µCi | Sr-82 Precision % CV* | Sr-85 µCi | Sr-85 Precision % CV | Sr-82 Level µCi/ 30 mCi Rb-82 |
|---|---|---|---|---|---|
| 1 | 10.0077 | 0.42 | 9.9961 | 0.12 | 0.3336 |
| 2 | 4.9751 | 0.59 | 4.9431 | 0.17 | 0.1658 |
| 3 | 1.0106 | 1.31 | 0.9886 | 0.39 | 0.0337 |
| 4 | 0.4828 | 1.89 | 0.5015 | 0.55 | 0.0161 |
| 5 | 0.2539 | 2.61 | 0.2510 | 0.77 | 0.0085 |
| 6 | 0.1269 | 3.73 | 0.1259 | 1.10 | 0.0042 |
| 7 | 0.0515 | 5.86 | 0.0613 | 1.57 | 0.0017 |
| 8 | 0.0371 | 3.99 | 0.0314 | 1.27 | 0.0012 |
| 9 | 0.0172 | 5.32 | 0.0163 | 1.59 | 0.0006 |
| 10 | 0.0089 | 5.78 | 0.0089 | 1.69 | 0.0003 |
| 11 | 0.0045 | 4.20 | 0.0047 | 1.15 | 0.0001 |
| 12 | 0.0028 | 4.45 | 0.0027 | 1.25 | 0.0001 |

$${}^{*}CV = \left(\frac{\sqrt{\text{Net Counts}}}{\text{Net Counts}}\right) \times 100,$$

TABLE 3

Comparison of measurements by the CZT gamma detector or dose calibrator to the truth standard.

| | CZT Gamma Detector Sr-82 | | | Dose Calibrator Sr-82 | | |
|---|---|---|---|---|---|---|
| ID | µCi | Precision % CV* | Trueness % Error vs HPGe** | µCi | Precision % CV*** | Trueness % Error vs HPGe** |
| 1 | 7.8700 | 0.27 | −21.36 | 8.63 | 0.30 | −13.77 |
| 2 | 4.0687 | 0.38 | −18.22 | 4.29 | 0.36 | −13.77 |
| 3 | 0.8455 | 0.83 | −16.34 | 0.87 | 0.45 | −13.91 |
| 4 | 0.4185 | 1.17 | −13.32 | 0.43 | 1.81 | −10.94 |
| 5 | 0.2098 | 1.66 | −17.37 | 0.21 | 3.23 | −17.29 |
| 6 | 0.1025 | 2.37 | −19.23 | 0.11 | 0.00 | −13.32 |
| 7 | 0.0561 | 3.21 | 8.93 | 0.05 | 12.50 | −2.91 |
| 8 | 0.0283 | 4.52 | −23.72 | 0.02 | 43.30 | −46.09 |
| 9 | 0.0139 | 6.44 | −19.19 | 0.01 | 0.00 | −41.86 |
| 10 | 0.0069 | 9.13 | −22.47 | 0.01 | 43.30 | 12.36 |
| 11 | 0.0037 | 12.48 | −17.78 | −0.01 | −86.60 | −322.22 |
| 12 | 0.0023 | 16.01 | −17.86 | 0.00 | 86.60 | −100.00 |

$${}^{*}CV = \left(\frac{\sqrt{\text{Net Counts}}}{\text{Net Counts}}\right) \times 100,$$

$${}^{**}\% \text{ Error} = \frac{(CZT \text{ or } DC - HPGe)}{HPGe} \times 100,$$

$${}^{***}\left(\frac{SD}{\text{Mean}}\right) \times 100, n = 3$$

In the data above, counting times for the HPGe were adjusted to obtain good counting statistics with a maximum CV of approximately 6% as shown in table 2. These times varied from 30 minutes for the most radioactive sample to 19 h for the least radioactive sample. The Sr85/82 ratio of 1.0 is approximately that of an example strontium-rubidium generator at the end of its 42 day life starting from an initial ratio of approximately 0.5, which is an example expected range when using only p,4n material. The higher proportion of Sr-85 leads to more counts than for Sr-82 and the lower CVs seen in table 2.

Samples were measured with the CZT detector using the Sr Calibration function in the Bracco Cardiogen Service Application with a 600 s acquisition, which is the same as that used for the Sr-Level measurement during QC. Background was measured before the samples and corrected automatically by the infusion system for each Sr activity calculation. The % CV for the CZT detector data (Sr-82/85) was determined based on net counts and was <4% down to and including the Alert Limit (0.002) or a total Sr-82/85 content of 0.1 µCi and still only approximately 8% at a ratio of 0.0003 almost 10-fold lower.

For the Dose Calibrator, the reading of each sample was allowed to stabilize for approximately 30 s before recording the result. Samples measurements were repeated three times to obtain a standard deviation and CV. The results are recorded in table 3. Only the Sr-82 values are provided for the CZT and dose calibrator as the Sr-85 levels are derived from the Sr-82 values using a mathematical function. The dose calibrator and gamma detector data were collected using standard times (60 s and 600 s, respectively) as may be commercially used.

The data show that whereas both detection systems show a loss of precision as the radioactivity decreases the precision of the CZT detector is better than that of the dose calibrator. The Dose Calibrator and the CZT gamma detector have very similar precision at an Expiry Limit (ratio 0.01) at 42 days, when the Rb-82 denominator is the lowest. The CZT gamma detector has acceptable precision down to a Sr Level of 0.0003 (below an example Alert limit of 0.002), which is consistent with the counting statistics, e.g., sufficient counts are being recorded to achieve the desired precision and the loss of precision is uniform. In contrast, the dose calibrator lacks precision at radioactivity levels at, or lower than, the Alert Limit. This may be due in part to the fact that dose calibrators have limited measurement resolution of only 0.01 µCi, driven by the resolution of the display which cause rounding or truncation errors. Thus, independent of, and additive to, any inherent uncertainty in the measurement, the minimum change that can be displayed by a dose calibrator for a total Sr-82/85 dose of 0.05 (as for the Alert limit for a 30 mCi dose at 42 days) is 20%. It is clear that the CadmiumZincTelluride (CZT) gamma detector has much better counting statistics (precision) at low activity levels that the Dose Calibrator.

The trueness of the CZT gamma detector and dose calibrator measurements is recorded in table 3 relative to the truth standard of the HPGe data. The dose calibrator and the CZT detector exhibit a similar bias of approximately −15% relative to the HPGe down to the Alert limit. Below the Alert limit the trueness of the dose calibrator varies wildly but that of the CZT remains as before. The breakdown in trueness of the dose calibrator may be a result of the decreased and variable precision.

Example 3

To evaluate the capability of a gamma detector to perform system calibration and dose constancy protocols, a CZT gamma detector was tested under the following conditions:

i. in an activity range corresponding to example Sr levels using three Na-22 sources of approximately 0.04-10 μCi and
ii. in an activity range corresponding to ranges that may be observed during calibration and dose constancy using Rb-82 of approximately 15-1000 μCi (at 600-1000 s after eluting into an eluate-receiving container).

Three Na-22 sources of approximately 0.04, 0.6, and 7.7 μCi were counted for 4500, 300, and 120 seconds, respectively. The maximum individual error ranged from −5.6 to 7.3% and all results were within a specification of +/−10%. The linear fit of each set had an r squared>0.95.

For linearity by decay, the range of Rb-82 encountered was 4.1-727 μCi from end-of-elution doses of 9.6-44.2 mCi. The maximum individual error ranged from −4.47 to 6.3%, and all results were within a specification of +/−10%.

Figure 6:
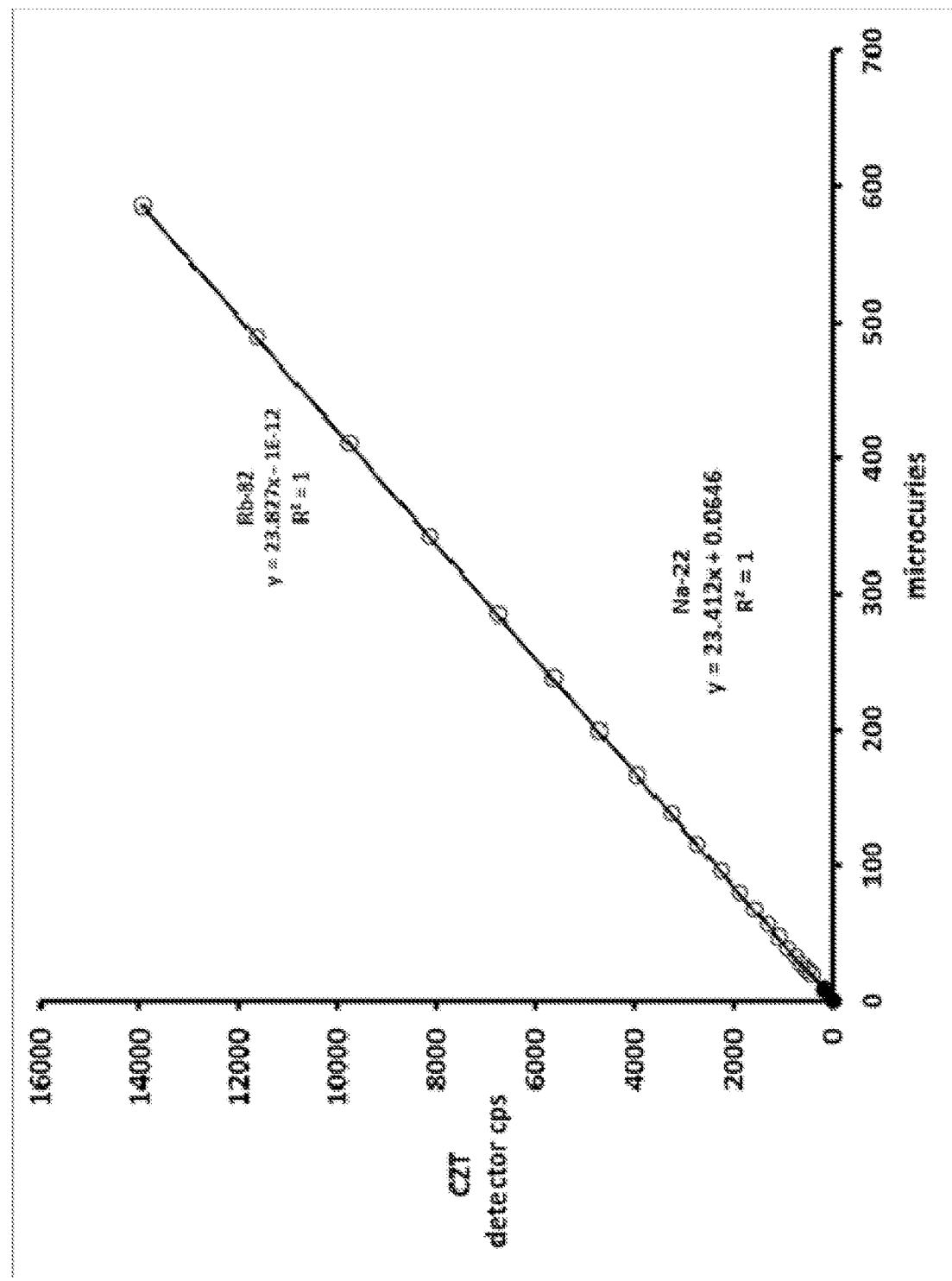
FIG. 6 illustrates linearity between activity and counts for an example gamma detector over a range of activities that may be observed in some example systems.

FIG. 6 illustrates the linearity between activity and counts for the example gamma detector over the full range of activities (Sr-level and calibration/dose constancy) that may be observed in some example systems. The fixed source and decay data for each system have the same slopes and intercepts as seen in the figure. The low activity Na-22 source data are the closed symbols and the high activity Rb-82 data the open symbols.

Given the excellent linearity over a wide range encompassing the doses expected and the accuracy of the gamma detector as calibrated against a NIST traceable standard, the data indicate that the gamma detector can be used to calibrate the dose delivery trueness/accuracy of the system.

Example 4

An experimental study was undertaken to determine if a predicted volume of eluate could be determined for a radioisotope generator at which an activity of a radioisotope in of interest will reach an end-of-life threshold. The experiment was performed using a infusion carts equipped with Sr-82/Rb-82 radioisotope generators. The carts were Bracco Model 1700 using a Cadmium Zinc Telluride (CZT) gamma detector.

As background, a Rubidium-82 (Rb-82) generator is a closed system used to produce rubidium Rb 82 chloride injection for intravenous use. Rubidium Rb 82 chloride injection is a radioactive diagnostic agent indicated for Positron Emission Tomography (PET) imaging of the myocardium under rest or pharmacologic stress conditions to evaluate regional myocardial perfusion in adult patients with suspected or existing coronary artery disease. An Rb-82 generator typically includes strontium Sr-82 adsorbed on a hydrous stannic oxide (or other suitable chromatographic support) column with an activity of approximately 90-150 millicuries Sr-82 at calibration time. In this instance the parent radionuclide is Sr-82 and the daughter radionuclide is Rb-82. Current FDA approved Rb-82 generators have temporal expiration limits of up to 60 days after the calibration date, governed in part by the half-life of the Sr-82 parent.

The approved generators also have expiration limits based on the Sr Level, which is the Sr-82 or Sr-85 uCi present in a dose divided by the Rb-82 mCi at End-of-Elution (EOE). There are currently three sets of Sr Level limit ratios used, from the FDA—Alert and Expiration/Expiry limits—and from the NRC—Legal limits. The current Legal and Expiration limits for Sr-82 are 0.02, and 0.01 μCi Sr-82/mCi Rb-82 respectively. The Alert limits are 0.002-0.004 μCi Sr-82/mCi Rb-82 depending on the temporal life of the generator. The Sr-85 ratios are 10-fold higher (0.2, 0.1 and 0.02/0.04 μCi/mCi respectively). Sr-85 is a radionuclidic contaminant of the Sr-82 and the higher allowable Sr Level ratios for Sr-85 were set when the Sr-85 was present at higher levels than they are today. Thus, in practice the Sr-85 Sr Levels cannot typically be reached before the Sr-82 Sr Levels. Nevertheless, the concepts and solutions provided here for Sr-82 also apply to Sr-85.

The Sr Level ratio reflects the chromatographic nature of the interaction between the two analytes, Sr and Rb, and the interaction of their radionuclides with the column material. As the interaction is chromatographic the point at which the ratio exceeds any of the Sr Level limits is a function of the total eluant volume passed through the generator column. As with classical chromatography there are slight differences in the interaction of the analytes with the column due to sample loading and column packing characteristics which mean that the volume at which a limit is reached varies slightly from generator to generator. In addition, if the rate of accumulation of total eluant is different, the day on which any of the limits may be reached will also be different.

Figure 7:
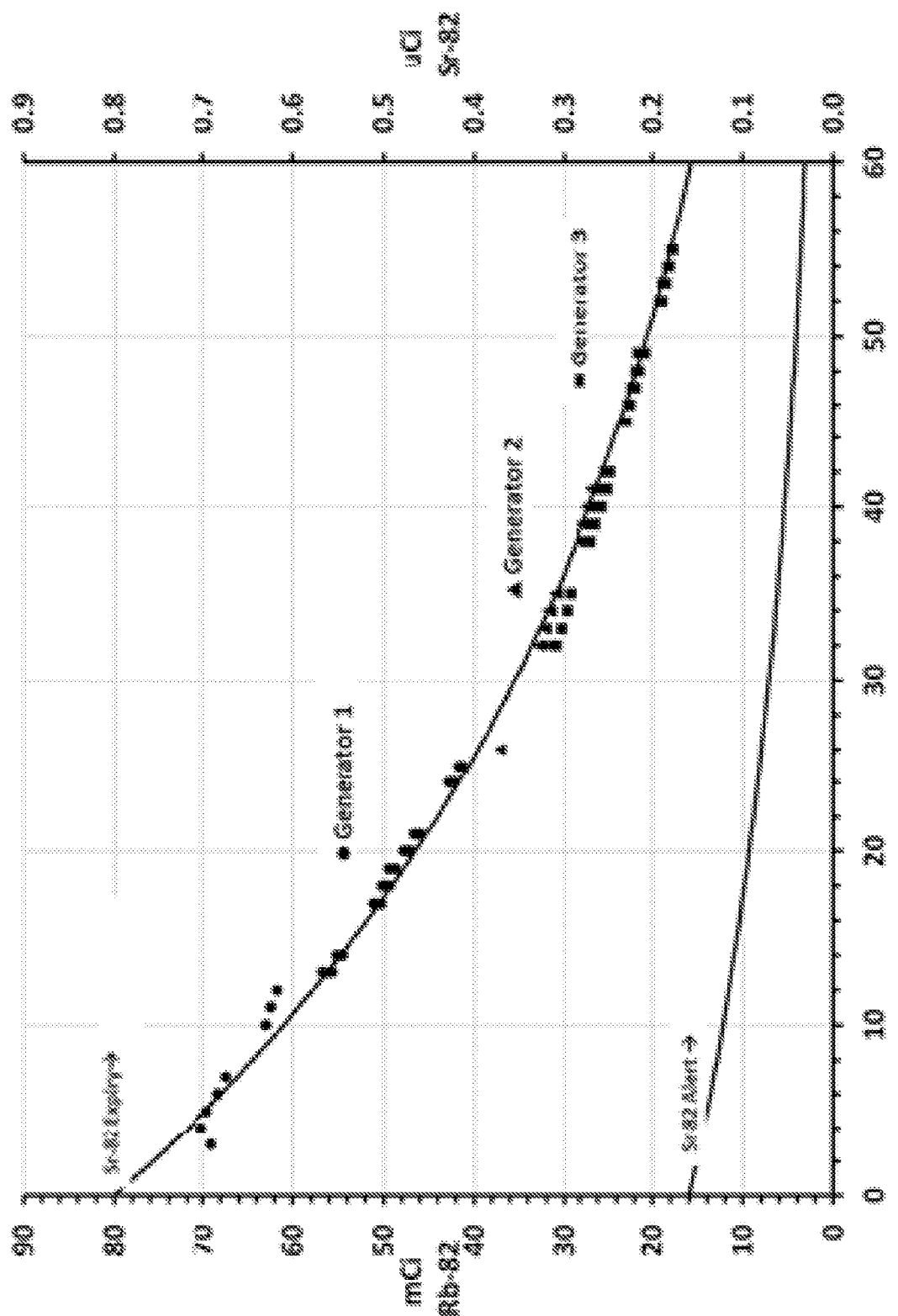
FIG. 7 is a plot of actual Rb-82 mCi collected as part of a Sr Level Test dose for five generators as a function of generator age.

The day on which a limit is reached influences the measurement not because of chromatographic principles but because of the different half-lives of the radionuclide analytes of Rb-82 (75 s), Sr-82 (25.34 days) and Sr-85 (64.85 days). Over the 42-60 day life of a generator the potency drops by a factor of ~3. The actual Rb-82 mCi in a Sr Level Test dose for three representative generators is plotted as a function of generator age in FIG. 7, left axis. They follow the expected exponential fit due to the decay of the Sr-82 parent. Knowing the Rb-82 mCi on a daily basis the Sr-82 uCi required to produce an Alert or Expiry ratio on each day can be calculated using the rearranged Sr Level equation and are shown in FIG. 7, solid lines, right axis.

Equation: $Sr\text{-}82_{uCi} = Rb\text{-}82_{mCi} \times Sr$ Level ratio (where Sr Level ratio=$0.002_{Alert}$ or $0.01_{Expiry}$)

The Sr-82 and Rb-82 relationships vs generator day have the same form because the two radionuclides are in secular equilibrium. On day 20, as an example, there are 0.09 & 0.46 uCi Sr-82 at the Alert and Expiry limit respectively and at day 42 there are 0.05 & 0.26 uCi Sr-82. Thus, as the generator ages the absolute amount of Sr-82 required for the Alert or Expiry limit drops with the same relationship as the Rb-82 and the accurate measurement of the Sr Level becomes more stringent.

A second issue is that the Sr Level Test, which must typically be performed as part of daily Quality Control before the generator is used to produce patient doses, is a single radioactivity measurement with associated uncertainty. The uncertainty depends in part on the precision and trueness of the detectors used to perform the test. ISO 5725 uses two terms "trueness" and "precision" to describe the accuracy of a measurement method. "Trueness" refers to the closeness of agreement between the arithmetic mean of a large number of test results and the true or accepted reference value. "Precision" refers to the closeness of agreement between test results. The general term 'accuracy' is used in ISO 5725 to refer to both trueness and precision.

Although the Sr Level is driven by classical chromatographic principles the actual performance of the system is non-classical as there are short periods of ≥10 min of no eluant flow, when the parent-daughter radionuclide pair are approaching secular equilibrium after prior use, and longer overnight or weekend periods of no eluant flow when no clinical work is performed. In addition, for the Sr Level test the rise of the Sr-82 chromatographic peak may be more important than the traditional peak maximum elution time (retention time) and at limit levels ~0.001% of the total Sr-82 on the column is in the test sample. The rate of change of an analyte that describes the shape of a chromatographic peak at these low analyte percentages is not a normal chromatographic parameter.

Thus the accuracy of the Sr Level Test is dependent on the day after calibration the test is performed, the uncertainty of the measurement system, and the variable chromatographic performance of the analytes.

Due to the variable and rapid rise in the Sr Level with increasing eluant volume near the Expiration limit and the uncertainty in the measurement it is possible that the Expiration limit can be reached during the day after a successful Sr Level Test. The requirement for the Alert limit by the FDA is a response to this and is an additional attempt to ensure that no patient receives a Rb-82 dose after the Expiration limit is reached. When the Alert limit is reached the user must typically perform additional quality Control testing after the passage of 750 mL eluant or after 4 patients have been dosed before additional patients can be dosed that day.

The employment of an additional test such as the Alert limit is detrimental because it takes time during the day to perform, uses some of the limited eluate volume that can be passed through the generator and increases radiation exposure to the user. It would be better to have a more accurate and reliable test for Sr Level.

Unexpectedly, we find that the increase in Sr radionuclides in the eluant leading to a rising Sr Level with eluant volume can be described, e.g., by fitting data to an exponential function. Furthermore, we find that the function can be used to predict the approach to the Expiration volume when applied to Sr Level data already collected. The Expiration volume determined using an exponential fit of the data uses multiple data points and benefits from the better statistics vs a single point measurement.

The accuracy of the predicted Expiration volume is dependent on the trueness and precision of the data set which is used as the input. This is reflected in both the approach to the actual volume as more data points are added and the final volume. We find that data collected using a non-ion-chamber gamma detector (e.g., CZT detector) are better than those collected using a dose calibrator because the non-ion-chamber gamma detector has better statistics.

Figure 8:
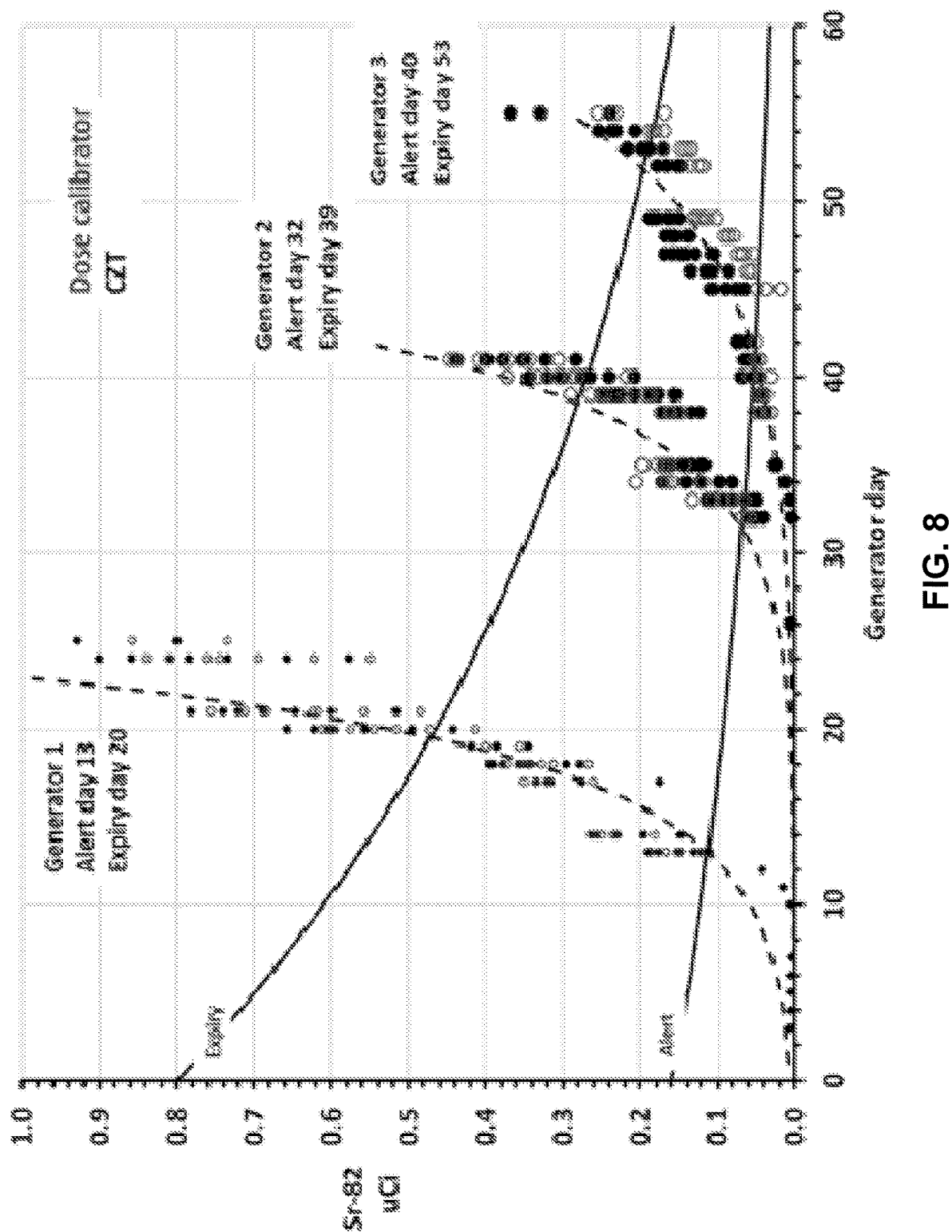
FIG. 8 is a plot of actual Sr-82 µCi data collected as part of a Sr Level test compared to the theoretical levels by day.

By way of example, in FIG. 8 the actual Sr-82 uCi data collected as part of the Sr Level test are compared to the theoretical levels by day (as shown in FIG. 7). These are paired data, the same sample was measured using a CZT detector and a dose calibrator. The solid black symbols are the CZT and the open blue symbols the dose calibrator data. The dashed lines are the exponential fit for the CZT data for all points above the first record of a 0.002 Sr Level. The Sr-82 uCi detected at the Alert and Expiry limits during the Sr Level test agree with the theoretical value for that day. The results for the two generators (1 & 2) which reached the Expiration limit before about day 40 are similar for the dose calibrator vs the CZT. The results for the cart (3) that reached the Expiration limit after about day 40 diverge because they are derived from the lowest Sr-82 levels and are collected in a region where the dose calibrator has already been demonstrated to have precision and trueness errors. The daily Quality Control results for generators 1, 2 & 3 are shown in FIG. 8. The lines are the best fit exponential functions using all the data.

These data were also progressively fit to an exponential function, starting with the first three paired samples collected and successively adding the next data point, and the Alert and Expiration volumes predicted. These are shown in Table 4, 5, and 6 and plotted in FIG. 9. For generator 1 and 2 both detectors predict the Expiration volume, as determined by fitting the whole CZT data set to an exponential function, with an error<750 mL from 3.5 L before the actual Expiration volume, and the goodness of fit ($r^2$) increases in a regular manner.

TABLE 4

Actual and predicted Expiration volumes for generator 1.

| Common | | | CZT | | | Dose Calibrator | | |
|---|---|---|---|---|---|---|---|---|
| | | | Predicted | Difference | | Predicted | Difference | |
| Days before | n | mL before | Expiry Volume (mL) | Predicted Expiry (mL) | Fit $r^2$ | Expiry Volume (mL) | Predicted Expiry (mL) | Fit $r^2$ |
| 8 | 3 | 4236 | 21096 | −813 | 0.995 | 21498 | 664 | 1.000 |
| 7 | 4 | 3465 | 21690 | −219 | 0.964 | 22190 | 28 | 0.965 |
| 6 | 5 | 2753 | 21751 | −158 | 0.977 | 22160 | 2 | 0.979 |
| 5 | 6 | 2141 | 21832 | −77 | 0.982 | 22170 | 8 | 0.986 |
| 4 | 7 | 1426 | 21915 | 6 | 0.985 | 22211 | 49 | 0.989 |
| 1 | 8 | 713 | 21972 | 63 | 0.988 | 22230 | 68 | 0.989 |
| 0 | 9 | 0 | 21909 | 0 | 0.990 | 22162 | 0 | 0.992 |

TABLE 5

Actual and predicted Expiration volumes for generator 2.

| | Common | | CZT | | | Dose Calibrator | | |
|---|---|---|---|---|---|---|---|---|
| Days before | n | mL before | Predicted Expiry Volume (mL) | Difference Predicted Expiry (mL) | Fit $r^2$ | Predicted Expiry Volume (mL) | Difference Predicted Expiry (mL) | Fit $r^2$ |
| 7 | 3 | 3535 | 19601 | 47 | 0.880 | 18792 | −505 | 0.940 |
| 6 | 4 | 2546 | 19730 | 176 | 0.945 | 19135 | −162 | 0.967 |
| 3 | 5 | 1833 | 19878 | 324 | 0.965 | 19878 | 581 | 0.965 |
| 2 | 6 | 1425 | 19856 | 302 | 0.975 | 19856 | 559 | 0.975 |
| 1 | 7 | 713 | 19719 | 165 | 0.981 | 19719 | 422 | 0.982 |
| 0 | 8 | 0 | 19554 | 0 | 0.983 | 19297 | 0 | 0.984 |

In contrast, the lower counts present in the generator 3 samples due to the longer days post calibration make the fits of both detector data poorer. The CZT results quickly converge and by 3 L before the actual Expiration volume have an error of <750 mL. In contrast, the dose calibrator results do not converge until much later and have volume errors>750 mL down to ~1 L before the actual Expiration volume with an inferior goodness of fit.

TABLE 6

Actual and predicted Expiration volumes for generator 3.

| | Common | | CZT | | | Dose Calibrator | | |
|---|---|---|---|---|---|---|---|---|
| Days before | n | mL before | Predicted Expiry Volume (mL) | Difference Predicted Expiry (mL) | Fit $r^2$ | Predicted Expiry Volume (mL) | Difference Predicted Expiry (mL) | Fit $r^2$ |
| 15 | 3 | 7081 | 30727 | 8918 | 0.940 | 8828 | −14905 | 0.941 |
| 14 | 4 | 6412 | 24331 | 2521 | 0.886 | −7860 | −31593 | 0.146 |
| 13 | 5 | 6120 | 22203 | 393 | 0.875 | 158531 | 134798 | 0.004 |
| 10 | 6 | 5596 | 21694 | −116 | 0.917 | 3245 | −20488 | 0.231 |
| 9 | 7 | 4708 | 21027 | −783 | 0.943 | 822829 | 799096 | 0.000 |
| 8 | 8 | 3821 | 20952 | −857 | 0.966 | 43858 | 20125 | 0.000 |
| 7 | 9 | 2897 | 21245 | −565 | 0.969 | 30387 | 6654 | 0.075 |
| 6 | 10 | 2285 | 21405 | −405 | 0.975 | 26820 | 3087 | 0.290 |
| 3 | 11 | 1673 | 21646 | −163 | 0.973 | 25293 | 1560 | 0.474 |
| 2 | 12 | 1215 | 21779 | −31 | 0.975 | 24497 | 764 | 0.602 |
| 1 | 13 | 657 | 21795 | −15 | 0.979 | 23907 | 174 | 0.685 |
| 0 | 14 | 0 | 21810 | 0 | 0.983 | 23733 | 0 | 0.746 |

These data were also fit to an exponential function using a binned approach of four data points, and the Alert and Expiration volumes predicted. These are shown in Tables 7, 8, and 9. As before, for generator 1 & 2 both detectors predict the Expiration volume, as determined by fitting the whole CZT data set to an exponential function, with an error<750 mL from 3.5 L before the actual Expiration volume, and the goodness of fit ($r^2$) being good.

TABLE 7

Actual and cumulative or binned predicted Expiration volumes for generator 1.

| | | | CZT | | | | | | Dose Calibrator | | | | | |
|---|---|---|---|---|---|---|---|---|---|---|---|---|---|---|
| | | | Predicted Expiry volume (mL) | | Difference Predicted Expiry volume (mL) | | Fit $r^2$ | | Predicted Expiry volume (mL) | | Difference Predicted Expiry volume (mL) | | Fit $r^2$ | |
| Days before | N | n | Cum. | Bin | Cum. | Bin | Cum. | Bin | Cum. | Bin | Cum. | Bin | Cum. | Bin |
| 8 | 3 | 4 | 21096 | 21690 | −813 | −219 | 0.995 | 0.964 | 21498 | 22190 | 664 | 28 | 1.000 | 0.965 |
| 7 | 4 | 4 | 21690 | 21998 | −219 | 89 | 0.964 | 0.969 | 22190 | 22345 | 28 | 183 | 0.965 | 0.955 |
| 6 | 5 | 4 | 21751 | 22037 | −158 | 128 | 0.977 | 0.948 | 22160 | 22329 | 2 | 167 | 0.979 | 0.925 |

TABLE 7-continued

Actual and cumulative or binned predicted Expiration volumes for generator 1.

| | | | CZT | | | | | | Dose Calibrator | | | | | |
|---|---|---|---|---|---|---|---|---|---|---|---|---|---|---|
| | | | Predicted Expiry volume (mL) | | Difference Predicted Expiry volume (mL) | | Fit $r^2$ | | Predicted Expiry volume (mL) | | Difference Predicted Expiry volume (mL) | | Fit $r^2$ | |
| Days before | N | n | Cum. | Bin | Cum. | Bin | Cum. | Bin | Cum. | Bin | Cum. | Bin | Cum. | Bin |
| 5 | 6 | 4 | 21832 | 21984 | −77 | 75 | 0.982 | 0.983 | 22170 | 22202 | 8 | 40 | 0.986 | 0.982 |
| 4 | 7 | 4 | 21915 | 21980 | 6 | 71 | 0.985 | 1.000 | 22211 | 22236 | 49 | 73 | 0.989 | 0.999 |
| 1 | 8 | 4 | 21972 | 22027 | 63 | 118 | 0.988 | 0.972 | 22230 | 22225 | 68 | 63 | 0.989 | 0.983 |
| 0 | 9 | 4 | 21909 | 21909 | 0 | 0 | 0.990 | 0.990 | 22162 | 22162 | 0 | 0 | 0.992 | 0.992 |

TABLE 8

Actual and cumulative or binned predicted Expiration volumes for generator 2.

| | | | CZT | | | | | | Dose Calibrator | | | | | |
|---|---|---|---|---|---|---|---|---|---|---|---|---|---|---|
| | | | Predicted Expiry volume (mL) | | Difference Predicted Expiry volume (mL) | | Fit $r^2$ | | Predicted Expiry volume (mL) | | Difference Predicted Expiry volume (mL) | | Fit $r^2$ | |
| Days before | N | n | Cum. | Bin | Cum. | Bin | Cum. | Bin | Cum. | Bin | Cum. | Bin | Cum. | Bin |
| 7 | 3 | 4 | 19601 | 19730 | 47 | 176 | 0.880 | 0.945 | 18792 | 19135 | −505 | −162 | 0.940 | 0.967 |
| 6 | 4 | 4 | 19730 | 19547 | 176 | −7 | 0.945 | 0.968 | 19135 | 19469 | −162 | 172 | 0.967 | 0.940 |
| 3 | 5 | 4 | 19878 | 20199 | 324 | 645 | 0.965 | 0.991 | 19878 | 19946 | 581 | 650 | 0.965 | 0.929 |
| 2 | 6 | 4 | 19856 | 19556 | 302 | 3 | 0.975 | 0.985 | 19856 | 19466 | 559 | 169 | 0.975 | 0.944 |
| 1 | 7 | 4 | 19719 | 19344 | 165 | −210 | 0.981 | 0.999 | 19719 | 19164 | 422 | −133 | 0.982 | 0.981 |
| 0 | 8 | | 19554 | | 0 | | 0.983 | | 19297 | | 0 | | 0.984 | |

As before, the lower counts present in the generator 3 samples due to the longer days post calibration make the fits of both detector data poorer. The CZT results converge but with more variability than with the cumulative data. As before, the dose calibrator results do not converge until much later and have larger volume errors and an inferior goodness of fit.

TABLE 9

Actual and cumulative or binned predicted Expiration volumes for generator 3.

| | | | CZT | | | | | | Dose Calibrator | | | | | |
|---|---|---|---|---|---|---|---|---|---|---|---|---|---|---|
| | | | Predicted Expiry volume (mL) | | Difference Predicted Expiry volume (mL) | | Fit $r^2$ | | Predicted Expiry volume (mL) | | Difference Predicted Expiry volume (mL) | | Fit $r^2$ | |
| Days before | N | n | Cum. | Bin | Cum. | Bin | Cum. | Bin | Cum. | Bin | Cum. | Bin | Cum. | Bin |
| 15 | 3 | 4 | 30777 | 24331 | 8918 | 2521 | 0.940 | 0.886 | 8828 | −7860 | −14905 | −31593 | 0.941 | 0.225 |
| 14 | 4 | 4 | 24331 | 20775 | 2521 | −1035 | 0.886 | 0.926 | −7860 | 29756 | −31593 | 6023 | 0.146 | 0.093 |
| 13 | 5 | 4 | 22203 | 20059 | 393 | −1751 | 0.875 | 0.968 | 158531 | 6826 | 134798 | −16906 | 0.004 | 0.031 |
| 10 | 6 | 4 | 21694 | 20211 | −116 | −1599 | 0.917 | 0.977 | 3245 | 33277 | −20488 | 9545 | 0.231 | 0.259 |
| 9 | 7 | 4 | 21027 | 20784 | −783 | −1025 | 0.943 | 0.984 | 822829 | 24374 | 799096 | 641 | 0.000 | 0.817 |
| 8 | 8 | 4 | 20952 | 21516 | −857 | −294 | 0.966 | 0.932 | 43858 | 21840 | 20125 | −1893 | 0.000 | 0.817 |
| 7 | 9 | 4 | 21245 | 22194 | −565 | 384 | 0.969 | 0.980 | 30387 | 23353 | 6654 | −380 | 0.075 | 0.897 |
| 6 | 10 | 4 | 21405 | 22654 | −405 | 845 | 0.975 | 0.962 | 26820 | 22480 | 3087 | −1253 | 0.290 | 0.998 |
| 3 | 11 | 4 | 21646 | 22337 | −163 | 527 | 0.973 | 0.954 | 25293 | 22600 | 1560 | −1132 | 0.474 | 0.996 |
| 2 | 12 | 4 | 21779 | 21779 | −31 | −31 | 0.975 | 0.903 | 24497 | 22590 | 764 | −1142 | 0.602 | 0.997 |
| 1 | 13 | 4 | 21795 | 22024 | −15 | 215 | 0.979 | 0.992 | 23907 | 23013 | 174 | −720 | 0.685 | 0.879 |
| 0 | 14 | | 21810 | | 0 | | 0.983 | | 23733 | | 0 | | 0.746 | |

The invention claimed is:

1. An infusion system comprising:
a radioisotope generator that generates a radioactive eluate via an elution,
an activity detector configured to measure an activity of a first radioisotope in the radioactive eluate generated by the radioisotope generator; and
a controller configured to:
track a cumulative volume of radioactive eluate generated by the radioisotope generator;
track the activity of the first radioisotope in the radioactive eluate generated by the radioisotope generator; and
determine a predicted volume of the radioactive eluate generated by the radioisotope generator at which the activity of the first radioisotope in the radioactive eluate will reach a threshold based on the tracked cumulative volume of the radioactive eluate and the tracked activity of the first radioisotope.

2. The infusion system of claim 1, wherein the radioactive eluate generated by the radioisotope generator comprises a second radioisotope with a shorter radioactive half-life than the first radioisotope.

3. The infusion system of claim 2, wherein the first radioactive radioisotope is a parent radioisotope and the second radioisotope is a decay product of the parent radioisotope.

4. The infusion system of claim 2, wherein the first radioactive radioisotope is strontium-82 and the second radioisotope is rubidium-82.

5. The system claim 1, wherein the controller is configured to determine the predicted volume by at least determining a relationship between the tracked cumulative volume of radioactive eluate and the tracked activity of the first radioisotope and determine the predicted volume at the threshold according to the relationship.

6. The system of claim 5, wherein the relationship is a curve, and the controller is configured to determine the predicted volume at the threshold at least by extrapolating the curve to the threshold.

7. The system of claim 1, wherein the controller is configured to control the infusion system to prevent a patient infusion procedure if the cumulative volume of radioactive eluate generated by the radioisotope generator exceeds the predicted volume.

8. The system of claim 1, wherein the controller is configured to issue a user alert if the cumulative volume of radioactive eluate generated by the strontium-rubidium radioisotope generator equals or exceeds the predicted volume.

9. The system of claim 1, wherein the threshold is a strontium-82 activity less than 0.02 µCi.

10. The system of claim 1, wherein the controller is configured to determine the predicted volume a plurality of times, each time in response to receiving new data concerning the cumulative volume of radioactive eluate generated by the radioisotope generator and the activity of first radioisotope in the radioactive eluate generated by the radioisotope generator.

11. The system of claim 1, wherein the activity detector comprises a gamma detector, and further comprising a frame that carries the gamma detector, the controller, and the radioisotope generator.

12. The system of claim 11, wherein the gamma detector is positioned to measure the gamma emissions emitted from a static portion of radioactive eluate.

13. The system of claim 11, further comprising an infusion tubing line, an eluate-receiving container, and a beta detector,
wherein the eluate-receiving container is in fluid communication with the infusion tubing line, and the infusion tubing line is configured to receive the radioactive eluate, either directly or indirectly, from the radioisotope generator,
the beta detector is positioned to measure the beta emissions emitted from the radioactive eluate flowing through the infusion tubing line; and
the gamma detector is positioned to measure the gamma emissions emitted from the static portion of the radioactive eluate in the eluate-receiving container.

14. The system of claim 13, further comprising:
an eluant reservoir containing an eluant;
a pump coupled to the eluant reservoir via an eluant line;
a waste container; and
an infusion tubing circuit that includes the infusion tubing line, an eluate line, a waste line, and one or more valves, wherein the infusion tubing line is in fluid communication with the eluate line via the one or more valves and the waste line is in fluid communication with the eluate line via the one or more valves,
wherein the controller is configured to control filling of the eluate-receiving container by controlling the pump and the one or more valves.

15. The system of claim 14, wherein the controller is further configured during a quality control process to:
control the pump to pump the eluant through the radioisotope generator and generate the radioactive eluate,
determine a radioactive activity of the radioactive eluate based on the beta emissions measured via the beta detector while the radioactive eluate is directed to the waste container,
upon the radioactive activity of the radioactive eluate reaching a threshold level of rubidium activity, control the one or more valves to place the infusion tubing line in fluid communication with the eluate line,
further control the pump to fill the eluate-receiving container with the radioactive eluate,
control the gamma detector to detect the gamma emissions from the radioactive eluate in the eluate-receiving container after a period of time sufficient for substantially all rubidium in the radioactive eluate to decay, and
determine the activity of the first radioisotope in the eluate-receiving container based on the gamma emissions measured by the gamma detector.

16. The system of claim 1, wherein the activity detector comprises a dose calibrator configured to receive a sample of radioactive eluate and determine the activity of the first radioisotope in the sample of radioactive eluate, and wherein the controller is communicatively coupled to the dose calibrator and configured to track the activity of the first radioisotope by storing in a non-transitory computer readable memory associated with the controller the activity of the first radioisotope determined by the dose calibrator.

17. The system of claim 1, wherein the controller is configured to track the cumulative volume of radioactive eluate generated by the radioisotope generator by receiving a signal from a volume sensor indicative of a volume of radioactive eluate generated by the radioisotope generator or by tracking operation of a pump of known capacity, and by storing in a non-transitory computer readable memory associated with the controller the tracked cumulative volume of radioactive eluate.

18. The infusion system of claim 1, further comprising radioactive shielding surrounding the activity detector and the radioisotope generator, the radioactive shielding providing a barrier effective to reduce radiation emitted by the radioisotope generator and the radioactive eluate below a limit allowable for operating personnel.

19. The infusion system of claim 1, wherein the controller is configured to track the cumulative volume of radioactive eluate generated by the radioisotope generator over a first period of time and track the activity of the first radioisotope in the radioactive eluate generated by the radioisotope generator over a second period of time.

20. The infusion system of claim 19, wherein the first period of time is the service-life-to-date of the strontium-rubidium radioisotope generator.

21. A method comprising:
pumping an eluant through a radioisotope generator of an infusion system and thereby generating a radioactive eluate via elution;
measuring an activity of a first radioisotope in the radioactive eluate generated by the radioisotope generator with an activity detector;
tracking, with one or more processors, a cumulative volume of radioactive eluate generated by the radioisotope generator;
tracking, with one or more processors, the activity of the first radioisotope in the radioactive eluate generated by the radioisotope generator; and
determining, with the one or more processors, a predicted volume of the radioactive eluate generated by the radioisotope generator at which the activity of the first radioisotope in the radioactive eluate will reach a threshold based on the tracked cumulative volume of the radioactive eluate and the tracked activity of the first radioisotope.

22. The method of claim 21, wherein the radioactive eluate generated by the radioisotope generator comprises a second radioisotope with a shorter radioactive half-life than the first radioisotope.

23. The method of claim 21, wherein the first radioactive radioisotope is strontium-82 and the second radioisotope is rubidium-82.

24. The method of claim 21, wherein determining, with the one or more processors, the predicted volume of the radioactive eluate comprises determining a relationship between the tracked cumulative volume of radioactive eluate and the tracked activity of the first radioisotope and determine the predicted volume at the threshold according to the relationship.

25. The method of claim 24, wherein the relationship is a curve, and determining, with the one or more processors, the predicted volume of the radioactive eluate comprises determining the predicted volume at the threshold at least by extrapolating the curve to the threshold.

26. The method of claim 21, further comprising controlling, by the one or more processors, the infusion system to prevent a patient infusion procedure if the cumulative volume of radioactive eluate generated by the radioisotope generator exceeds the predicted volume.

27. The method of claim 21, further comprising replacing the radioisotope generator with a replacement radioisotope generator if the cumulative volume of radioactive eluate generated by the radioisotope generator is within a threshold amount of the predicted volume.

28. The method of claim 21, wherein the threshold is a strontium-82 activity value within a range from 0.002 µCi to 0.02 µCi.

29. The method of claim 21, wherein determining, with the one or more processors, the predicted volume of the radioactive eluate comprises determining the predicted volume a plurality of times, each time in response to receiving new data concerning the cumulative volume of radioactive eluate generated by the radioisotope generator and the activity of first radioisotope in the radioactive eluate generated by the radioisotope generator.

30. The method of claim 21, wherein the activity detector is a non-ion-chamber gamma detector.

31. The method of claim 21, wherein the activity detector is a dose calibrator.

32. The method of claim 21, wherein tracking, with one or more processors, the cumulative volume of radioactive eluate generated by the radioisotope generator comprises receiving, by the one or more processors, a signal from a volume sensor indicative of a volume of radioactive eluate generated by the radioisotope generator or tracking operation of a pump of known capacity, and by storing in a non-transitory computer readable memory associated with the one or more processors the tracked cumulative volume of radioactive eluate.

* * * * *